United States Patent
Homayounfar et al.

(10) Patent No.: US 11,931,159 B2
(45) Date of Patent: Mar. 19, 2024

(54) WEARABLE TEXTILE-BASED HYDROGEL ELECTRODE FOR MEASURING BIOPOTENTIAL

(71) Applicant: University of Massachusetts, Boston, MA (US)

(72) Inventors: Seyedeh Zohreh Homayounfar, Amherst, MA (US); Ali Kiaghadi, Amherst, MA (US); Soha Rostaminia, Amherst, MA (US); Deepak Ganesan, Amherst, MA (US); Trisha L. Andrew, Amherst, MA (US)

(73) Assignee: University of Massachusetts, Boston, MA (US)

( * ) Notice: Subject to any disclaimer, the term of this patent is extended or adjusted under 35 U.S.C. 154(b) by 517 days.

(21) Appl. No.: 17/091,675

(22) Filed: Nov. 6, 2020

(65) Prior Publication Data
US 2021/0137402 A1    May 13, 2021

Related U.S. Application Data

(60) Provisional application No. 62/932,936, filed on Nov. 8, 2019.

(51) Int. Cl.
*A61B 5/00* (2006.01)
*A61B 5/05* (2021.01)
*A61B 5/24* (2021.01)
*A61B 5/398* (2021.01)

(52) U.S. Cl.
CPC ............ *A61B 5/398* (2021.01); *A61B 5/2415* (2021.01); *A61B 5/6814* (2013.01); *A61B 5/6833* (2013.01); *A61B 5/688* (2013.01); *A61B 2562/0215* (2017.08)

(58) Field of Classification Search
CPC ............ A61B 5/259; A61B 2562/0215; A61B 2562/125; A61B 5/411; A61B 5/282; A61B 5/6833; A61B 5/25; A61B 5/6831; A61B 2560/0412; A61B 5/6804; A61B 5/6802; A61B 5/24; A61B 5/291; A61B 5/296; A61B 2562/0217; A61N 1/0492; A61N 1/048; A61N 1/0496
USPC ......... 600/372, 382–393, 508–509, 544–545
See application file for complete search history.

(56) References Cited

U.S. PATENT DOCUMENTS

| | | | |
|---|---|---|---|
| 8,275,441 B2 * | 9/2012 | Copp ................... | A61N 1/0496 607/152 |
| 2006/0183989 A1 * | 8/2006 | Healy ...................... | A61B 5/24 607/152 |
| 2016/0095527 A1 * | 4/2016 | Thng ...................... | A61B 5/339 600/382 |

* cited by examiner

*Primary Examiner* — Joseph A Stoklosa
*Assistant Examiner* — Brian M Antiskay
(74) *Attorney, Agent, or Firm* — Schwegman Lundberg & Woessner, P.A.

(57) ABSTRACT

A textile-based hydrogel electrode comprises a textile-based backing layer, a conductive structure coupled to the textile-based backing layer, and a hydrogel body in contact with at least a first portion of the conductive structure, wherein the first portion of the conductive structure and the hydrogel body form an ionic interface configured to generate an electrical signal through the conductive structure corresponding to a biopotential change proximate to the textile-based hydrogel electrode.

20 Claims, 19 Drawing Sheets

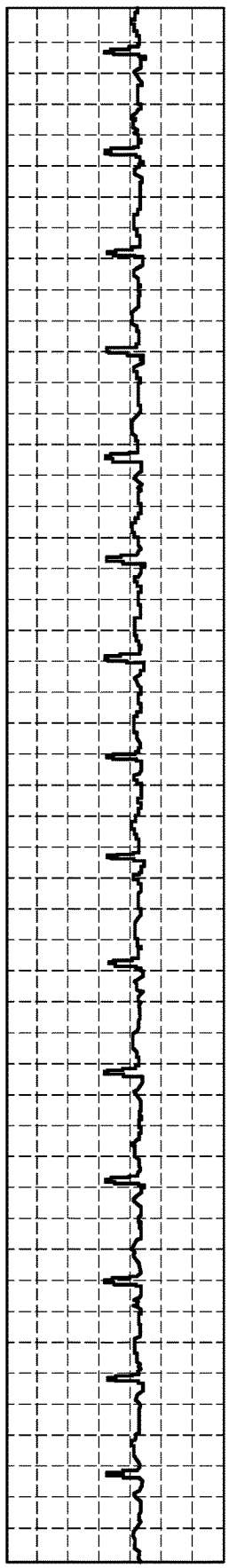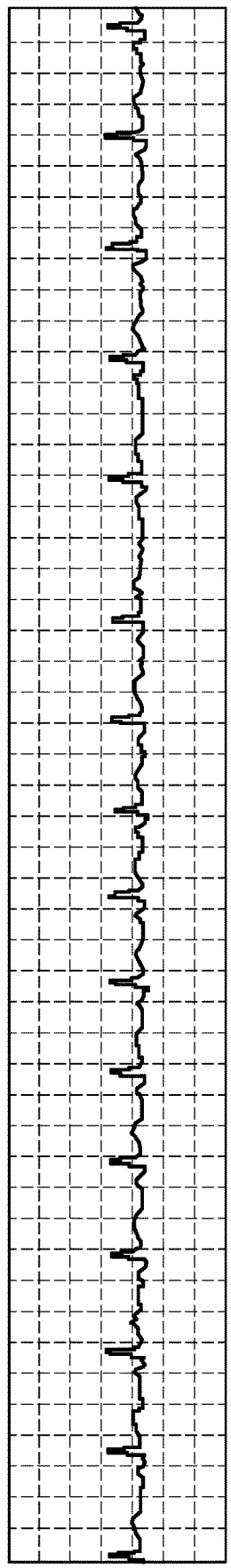
FIG. 18A
FIG. 18B

WEARABLE TEXTILE-BASED HYDROGEL ELECTRODE FOR MEASURING BIOPOTENTIAL

CROSS-REFERENCE TO RELATED APPLICATION

This application claims the benefit of priority to U.S. Provisional Patent Application Ser. No. 62/932,936 entitled "WEARABLE BIMODAL ELECTRODE ARRAY FOR ELECTRO-OCULOGRAPHY," filed Nov. 8, 2019, the disclosure of which is incorporated by reference herein in its entirety.

BACKGROUND

Eye tracking with a wearable device is usable in different sorts of applications; e.g. medical applications such as determination of visual fatigue, sleep studies, and diagnosing a variety of disease states; as well as human computer interface applications, such as for security or military applications or for the gaming industry. Video-based eye trackers—currently the most common method of eye-movement detection—use one or more cameras mounted on a headset to record images or video of the user's eye, and then the images or video are processed to calculate a gaze position. Due to the considerable computational power cost, video-based eye trackers cannot be practically used in portable, battery based, long term applications.

Electro-oculography (EOG) has been considered as an alternative to video-based eye tracking devices. EOG has been theorized as potentially being a more convenient wearable device, with the ability to be made more lightweight, accurate, and with lower power consumption compared to video-based eye trackers.

SUMMARY

The present disclosure describes a system and method for measuring or tracking one or more electrophysiological properties within a body, and in particular within a human body. In particular, the systems and methods described herein provide for measurement or tracking of one or more electrophysiological properties comprising a biopotential change that can be measured with an electrode that is external to the body but that can be placed in contact with or in close proximity to the body, such as an electrode that can be placed in contact with a subject's skin proximate to an area of interest. For example, the present disclosure describes a system and method for measuring or tracking eye movement using electro-oculography ("EOG") with one or more electrodes placed on or near a subject's skin in close proximity to the subject's eye.

In an example, the present disclosure describes a textile-based hydrogel electrode comprising a textile-based backing layer, a conductive structure coupled to the textile-based backing layer, and a hydrogel body in contact with at least a first portion of the conductive structure, wherein the first portion of the conductive structure and the hydrogel body form an ionic interface configured to generate an electrical signal through the conductive structure corresponding to a biopotential change proximate to the textile-based hydrogel electrode.

In another example, the present disclosure describes a method of manufacturing a textile-based hydrogel electrode, the method comprising the steps of coupling a conductive structure to a textile-based backing layer, and depositing a hydrogel material onto the conductive structure to form a hydrogel body that is in contact with a specified portion of the conductive structure, wherein the specified portion of the conductive structure comprises a first material that ionically interacts with the hydrogel material to form an ionic interface between the hydrogel body and the conductive structure, and wherein the ionic interface is configured to generate an electrical signal through the conductive structure corresponding to a biopotential change proximate to the ionic interface.

In yet another example, the present disclosure describes a wearable biopotential measuring device comprising a support scaffold configured for wearing by a subject, and a plurality of textile-based hydrogel electrodes coupled to the scaffold so that when the support scaffold is worn by the subject, each of the plurality of textile-based hydrogel electrodes are positioned proximate to a corresponding specified bodily structure of the subject, wherein each of the plurality of textile-based hydrogel electrodes is configured to generate an electrical signal corresponding to a biopotential change of the corresponding specified bodily structure. In an example, at least one of the textile-based hydrogel electrodes comprises a textile-based backing layer, a conductive structure coupled to the textile-based backing layer, and a hydrogel body in contact with at least a first portion of the conductive structure, wherein the first portion of the conductive structure and the hydrogel body form an ionic interface that is configured to generate the electrical signal corresponding to the biopotential change of the corresponding specified bodily structure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 11A-1D are bar graphs of the signal amplitudes of the example textile-based hydrogel electrode of FIG. 3, the conventional wet electrode, and the dry silver-plated fabric electrode for the movement artifacts of various head motions by the wearer, in accordance with various embodiments of the present disclosure.

FIGS. 18A and 18B are graphs of the electrocardiography signal captured by the example textile-based hydrogel electrode of FIG. 3 and a commercial electrode, respectively, as measured through a commercial three-lead heart monitoring device, in accordance with various embodiments of the present disclosure.

DETAILED DESCRIPTION

Figure 1:
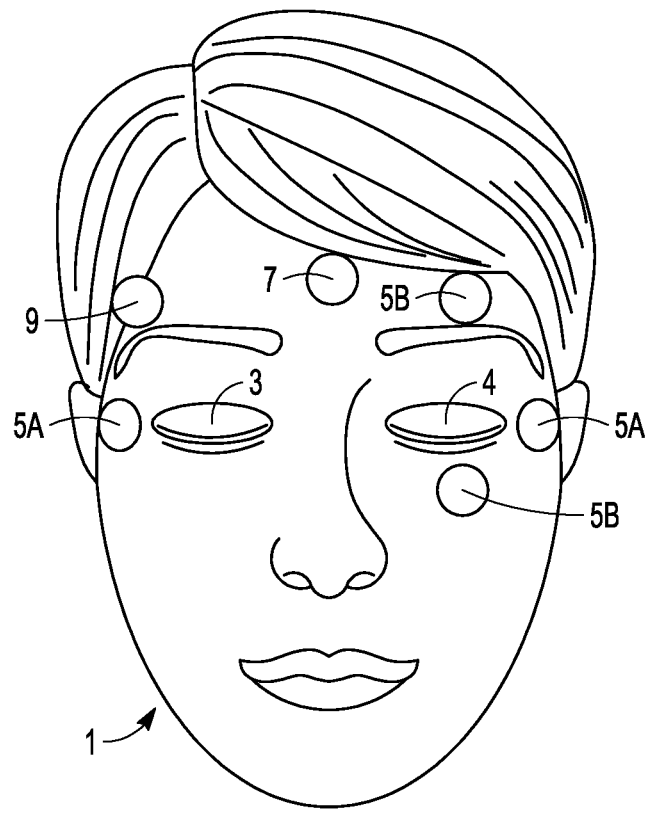
FIG. 1 is front view of a person showing example locations for placement of electro-oculography electrodes and a pulse sensor location, in accordance with various embodiments of the present disclosure.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The example embodiments may be combined, other embodiments may be utilized, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

References in the specification to "one embodiment", "an embodiment," "an example embodiment," "an example," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range. The statement "about X to Y" has the same meaning as "about X to about Y,'" unless indicated otherwise. Likewise, the statement "about X, Y, or about Z" has the same meaning as "about X, about Y, or about Z," unless indicated otherwise.

In this document, the terms "a" or "an" are used to include one or more than one and the term "or" is used to refer to a nonexclusive "or" unless otherwise indicated. Unless indicated otherwise, the statement "at least one of" when referring to a listed group is used to mean one or any combination of two or more of the members of the group. For example, the statement "at least one of A, B, and C" can have the same meaning as "A; B; C; A and B; A and C; B and C; or A, B, and C," or the statement "at least one of D, E, F, and G" can have the same meaning as "D; E; F; G; D and E; D and F; D and G; E and F; E and G: F and G; D, E, and F; D, E, and G; D, F, and G; E, F, and G; or D, E, F, and G." A comma can be used as a delimiter or digit group separator to the left or right of a decimal mark; for example, "0.000,1'" is equivalent to "0.0001."

In the methods described herein, the steps can be carried out in any order without departing from the principles of the invention, except when a temporal or operational sequence is explicitly recited. For example, a recited act of doing X and a recited act of doing Y can be conducted simultaneously within a single operation, and the resulting process will fall within the literal scope of the process. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, within 1%, within 0.5%, within 0.1%, within 0.05%, within 0.01%, within 0.005%, or within 0.001% of a stated value or of a stated limit of a range, and includes the exact stated value or range.

The term "substantially" as used herein refers to a majority of, or mostly, such as at least about 50%, 60%, 70%, 80%, 90%, 95%, 96%, 97%, 98%, 99%, 99.5%, 99.9%, 99.99%, or at least about 99.999% or more, or 100%.

In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Electrophysiological Sensing

The present disclosure describes a wearable device for accurate measurement of electrical activity corresponding to one or more electrophysiological processes of the body of the wearer. For example, as described in more detail below, the present disclosure describes a wearable device for accurate measurement of electrical activity corresponding to a change in biopotential for one or more tissues or physiological structures of a subject. The wearable device can include a textile-based hydrogel electrode to measure the biopotential change of interest.

As used herein, the term "textile" or "textile-based," when referring to the substrate that forms one or more structures of an electrode, such as the hydrogel electrode described in more detail below, refers to a structure comprising one or more fibrous structures, and in particular to threading or thread-like structures (such as yarns, threads, and the like), arranged to collectively form a bendable, sheet-like layer of cloth or cloth-like material (such as by weaving or otherwise combining the one or more fibrous structures into a cloth layer). "Textiles" commonly refers to materials that form the cloth layers of a garment or other apparel, although the present description is not limited merely to "textiles" that are typically used for garment or apparel fabrication. That being said, in some examples, the substrates that are used to form each of the sensors may be a conventional, off-the-shelf woven or non-woven fabric.

In an example, the textile-based hydrogel electrode described herein is configured to generate an electrical signal corresponding to a biopotential change in one or more tissues or bodily structures, for example by generating an electrical signal with a magnitude that is proportional or otherwise related to a voltage across the one or more tissues or bodily structures. A specific example of an electrophysiological signal that can be generated by the textile-based hydrogel electrode described herein is an electrooculogram signal corresponding to a corneo-retinal standing potential for a subject's eye. Measurement of the electrooculogram signal, which is referred to as electrooculography (or "EOG"), is described in more substantial detail below.

The inventors have also used the textile-based electrode described herein for generating other electrophysiological signals, including an electroencephalogram corresponding to neurological electrical activity, e.g., as measured by electroencephalography (or "EEG") and an electromyogram corresponding to electrical activity of one or more muscles, e.g., as measured by electromyography ("EMG"). Those having skill in the art will appreciate that the textile-based hydrogel electrode described herein may be used to generate still other electrophysiological signals as measured by other currently-known or later-discovered methods of electrophysiological monitoring, and in particular to those methods involving an electrode placed in contact with or proximate to a subject's skin. These other electrophysiological signals and methods can include, but are not limited to: an electrocardiogram measured by electrocardiography ("ECG" or "EKG"); an electronystagmogram measured by electronystagmography; an electro-olfactogram measured by electro-olfactography; an electrocochleogram measured by non-invasive electrocochleography; an electrogastrogram measured by electrogastrography; an electrogastroenterogram measured by electrogastroenterography; an electroglottogram measured by electroglottography; an electrodermograph measured by electrodermography; or an electroneurogram measured by electroneurography.

Electro-Oculography

Electro-oculography (hereinafter "EOG") involves measuring the corneo-retinal standing biopotential that naturally occurs between the front and the back of the human eye, which can be modeled as a constant electrical dipole. Eyeball rotation leads to the change in the dipole orientation, which subsequently gives rise to the change in the EOG signal amplitude. In an example, the signal can be measured through two pairs of electrodes located in periorbital positions close to the eyes with respect to a ground electrode. In an example, EOG has been theorized as an alternative to video-based eye tracking.

FIG. 1 shows a subject 1 (also referred to herein as "the wearer 1") and a set of electrodes 5A, 5B configured to detect EOG signals (also referred to hereinafter as "EOG electrodes 5A, 5B" or collectively as "EOG electrodes 5" or simply "electrodes 5"). A first set of the electrodes 5A are placed horizontally adjacent to the eyes 3 of the wearer 1, referred to as the "horizontal channel electrodes 5A", and a second set of the electrodes 5B positioned vertically above and below one of the subject's eyes, referred to as the "vertical channel electrodes 5B." In an example, the electrodes 5A, 5B are placed in periorbital positions proximate to the eyes 3 of the wearer 1. A ground electrode 7 can also be positioned on the face of the wearer 1, such as on the forehead as shown in FIG. 1. In an example, a pulse sensor 9 can also be included, which can be positioned in the approximate region of the wearer's supraorbital artery.

For applications involving measuring electrical signals from a living organism such as a human, including EOG, there is typically a tradeoff between comfort for the wearer 1 and signal detection with a high signal-to-noise ratio. Wet gel-based electrodes have typically been used to improve signal acquisition. However, conventional gel-based Ag/AgCl electrodes typically require an uncomfortable skin adhesive that is not aesthetically pleasing and is not practical for continuous wear on the face in close proximity to the eyes 3 of the wearer 1. In addition, since the signal decays irrecoverably once the gel is dried out, these wet electrodes typically are not reusable and cannot be applied for long-term applications In order to avoid these problems with gel-based electrodes, attempts have been made to produce wearable devices with dry electrodes for EOG signal detection. However, devices with dry electrodes were known to give rise to motion artifacts and erratic signals when the wearer is talking, chewing or moving their head. Motion artifacts can be so severe that they have made EOG devices with dry electrodes unreliable for measure EOG signals.

Other attempts have been made to make yarn or textile-based electrodes for the purpose of measuring EOG signals. One study integrated a silver-coated fabric into a head cap and an eye mask to be used as a dry electrode for EOG and facial EMG measurements. Another study used an electrically conductive polyurethane foam covered by a conductive fabric to detect EEG/EOG signals through both polarization and conductivity.

Unfortunately, none of these previous efforts have provide for accurate long-term monitoring in a comfortable design with low motion artifacts caused by ordinary activity. In particular, because the electrodes must be positioned close to the subject's eyes to obtain accurate EOG measurements, the design of electrodes that are comfortable and capable of damping motion artifacts in order to provide for efficient data acquisition is of great importance.

Electro-Oculography System

The present disclosure describes a wearable device for accurate measurement of electrical activity corresponding to eye movement by the wearer, also referred to as an "eye tracking device." In an example, the device includes two kinds of embedded sensors—(1) a textile-based hydrogel electrode to measure biopotential changes (such as by generating an electrical signal for EOG; and (2) a textile-based pressure sensor for pulse detection. As described above, the terms "textile" or "textile-based" can refer to a structure that forms one or more layers of the hydrogel electrode or the pressure sensor and/or the overall eye tracking device comprising one or more fibrous structures such as threading or thread-like structures (for example yarns, threads, and the like) arranged to collectively form a bendable, sheet-like layer of cloth or cloth-like material, such as by weaving or otherwise combining the one or more fibrous structures into a cloth layer The two textile-based sensors that can simultaneously perform eye tracking and pulse monitoring while being comfortable and durable enough to be readily adopted into daily life. The textile-based electrodes successfully address known drawbacks of conventional "wet" electrodes, in addition to affording high signal to noise ratio during long-term data acquisition, displaying wash-stability, breathability, little to no skin irritation, and being capable of further miniaturization for embedding into other wearable platforms. The fabric-based pressure sensor similarly displays wash stability, breathability and comfort while allowing for the wearer's pulse to be imperceptibly measured, simultaneously with any eye movement. The concept of a bimodal device, i.e., one that is capable of revealing more than one physiological metric at a time, has not been previously explored for eye tracking systems. The ability to track pulse provides a baseline metric for the wearer's physical state and stress level, which, when combined with eye movement enables a host of cutting-edge biomedical, psychological, and psycho-social studies, in addition to improving the accuracy and usability of gaming and virtual reality headsets.

Figure 2:
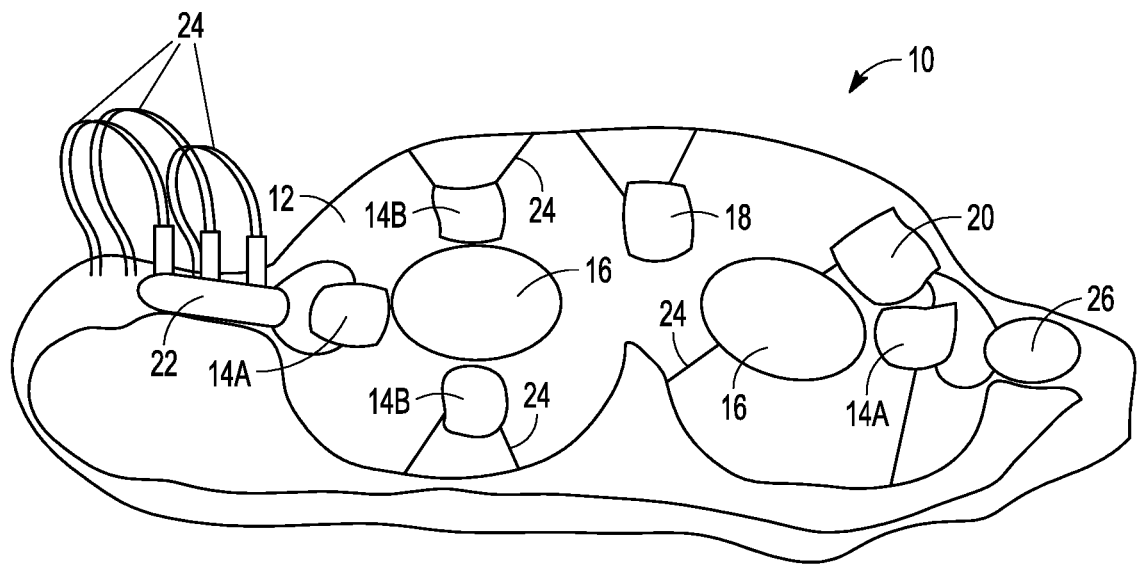
FIG. 2 is a rear view of an example wearable device with a plurality of textile-based hydrogel electrodes for measuring a biopotential of a wearer of the device, in accordance with various embodiments of the present disclosure.

FIG. 2 is a schematic view of an example device 10 for measuring electrical activity corresponding to one or more electrophysiological processes of the body of the wearer, such as to measure corneo-retinal biopotential via EOG for the purpose of tracking eye movement. The device 10 includes a supporting structure 12, also referred to as a "scaffold 12" for supporting electrodes and other electronics of the device 10. In an example, the scaffold 12 includes a tightly woven, a tightly knit, or a non-woven fabric having an area of at least about 0.5 inches by about 0.5 inches. In an example, the scaffold 12 is a commercially available eye mask, such as those sold as sleep masks. However, other scaffolds 12 could be used without varying from the scope of the present disclosure, including, but not limited to, goggles, glasses, a headband, a hat, and headphones.

The device 10 also includes a plurality of electrodes 14A, 14B, 18 coupled to the scaffold. In an example, one type of electrode used is a textile-based electrode configured to generate an electrical signal corresponding to a biopotential in the body of the wearer 1, such as a corneo-retinal biopotential corresponding to EOG measurement. For this reason, this type of electrode is also referred to hereinafter as an "EOG electrode." However, as noted above, the biopotential-measuring electrode that is referred to as "the EOG electrode" can also be configured for measuring biopotential for other purposes including, but not limited to, for electroencephalography (EEG), electromyography (EMG), or electrocardiography (ECG or EKG).

In the example shown in FIG. 2, five of the EOG electrodes are coupled to the scaffold 12 so that they will be proximate to the wearer's eyes. In an example, a set of two or more EOG electrodes 14A form the horizontal channel by being positioned horizontally proximate to eye holes 16 in the scaffold 12, such that when the device 10 is worn the EOG electrodes 14A will be positioned horizontally proximate the wearer's eyes (also referred to hereinafter as "horizontal channel EOG electrodes 14A" or simply as "horizontal channel electrodes 14A"). In an example, another set of two or more electrodes 14B form the vertical channel by being positioned vertically proximate to one of the eye holes 16 such that when the device 10 is worn the electrodes 14B will be positioned vertically proximate to the wearer's eye associated with that eye hole 16 (also referred to hereinafter as "vertical channel EOG electrodes 14B" or simply as "vertical channel electrodes 14B"). In an example, another EOG electrode 18 is used as a ground (also referred to hereinafter as "the ground electrode 18") which can be coupled to the scaffold 12 so that it will be located at the center of the wearer's forehead when the device 10 is worn. The horizontal and vertical channel electrodes 14A, 14B are positioned relative to the eye holes 16 so that they will be on opposite sides of the wearer's eyes in periorbital positions for the best measurement of corneo-retinal biopotential. In an example, a second type of electrode 20 is coupled to the scaffold 12, which is a fabric-based pressure sensing electrode 20 for measuring the wearer's pulse (also referred to hereinafter as "the pressure sensor electrode 20," "the pressure sensor 20," "the pulse sensor electrode 20," or "the pulse electrode 20"). In an example, the pressure sensor 20 is coupled to the scaffold 12 in a position so that it will be worn proximate to where the wearer's supraorbital artery is located when the device 10 is worn, e.g., so that the pressure sensor 20 will be at or proximate to the wearer's temple. In this position, the pressure in the supraorbital artery induced by heart contractions can be well detected, the detection of which gives accurate tracking of the wearer's heart rate.

The device 10 can also include one or more controller devices 22 (also referred to simply as "the controller 22"), which can send control signals to one or more of the electrodes 14A, 14B, 18, 20 and/or receive signal information from one or more of the electrodes 14A, 14B, 18, 20. The device 10 can also include wiring 24 to electrically connect the electrodes 14A, 14B, 18, 20 to the controller 22 and/or to a power source such as a battery 26.

Textile-Based Hydrogel Biopotential Electrode

Figure 3:
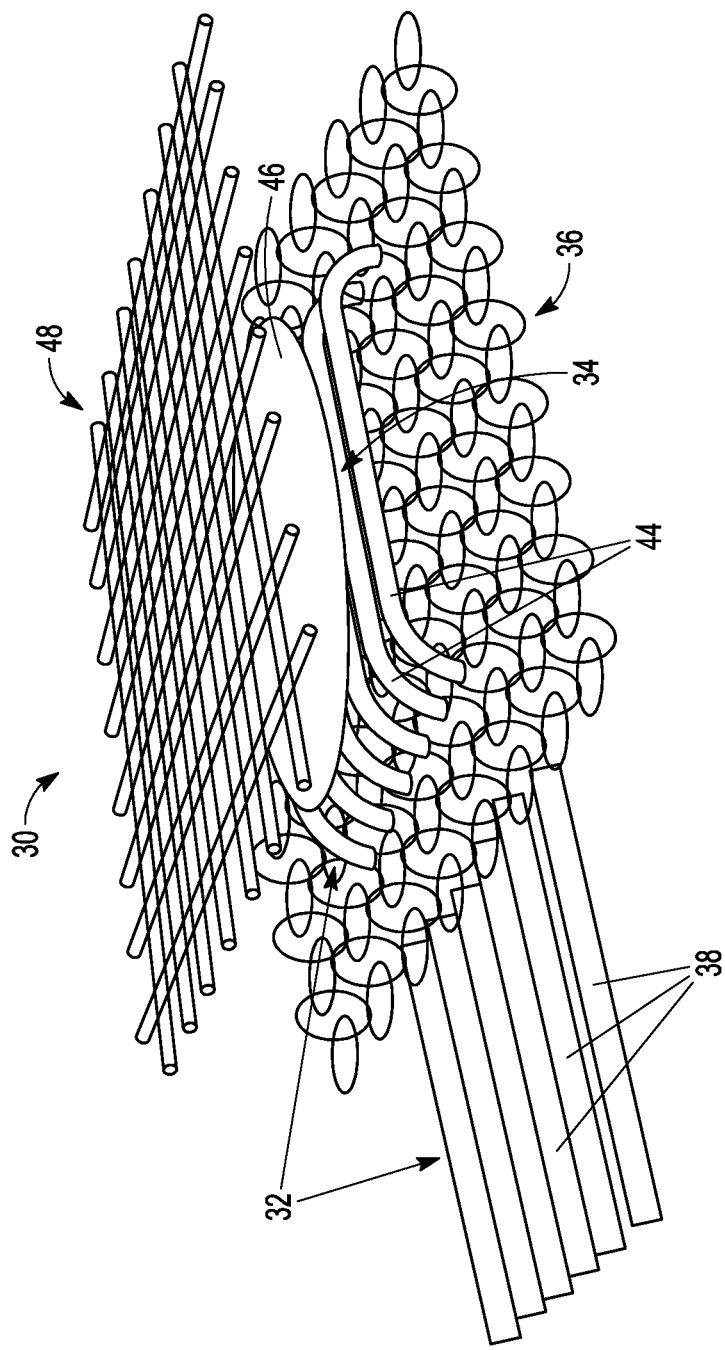
FIG. 3 is an exploded perspective view of an example textile-based hydrogel electrode, in accordance with various embodiments of the present disclosure.

In an example, each of the textile-based hydrogel electrodes 14A, 14B, 18 provide for the detection of biopotential using one or more commercial fabrics. As will be appreciated, the use of a commercially available fabric can provide a sense of comfort for the user as opposed to a feeling of having sticky patches on his or her skin, which can cause a feeling of distress. FIG. 3 is a schematic perspective view of an example of the textile-based hydrogel electrode 30 that can be used as, for example, one of the horizontal channel EOG electrodes 14A, one of the vertical channel EOG electrodes 14B, or as the ground electrode 18 in the wearable device 10 of FIG. 1. FIGS. 4A-4D show various steps of an example method of fabricating the example textile-based hydrogel electrode 30 shown in FIG. 3.

The textile-based hydrogel electrode 30 includes a conductive structure 32 with an ionic interface 34 to bridge between ionic charge in the wearer's body and the electric current flowing through one or more wires connected to the EOG electrode 30 (such as the wires 24 in the device 10 of FIG. 1). In an example, the conductive structure 32 comprises one or more metal-coated threads 38. In an example, a specified portion 40 of the conductive structure 32, such as a specified portion 40 of the one or more metal-coated threads 38 as shown in FIG. 3. In an example, the specified portion 40 of the conductive structure 32 comprises a material 44 that interacts with a hydrogel material (e.g., the material of the hydrogel body 46 described in more detail below) in order to form the ionic interface 34 (also referred to hereinafter as an "ionic interface material 44").

In an example, the conductive structure 32 and the ionic interface 34 have a relatively large surface area to maximize an area of contact with the wearer's skin. For this reason, the conductive structure 32 may also be referred to as a "conductive plate." The conductive plate 32 can be coupled to a textile-based backing layer 36, for example a fabric-based backing layer, such as a cotton backing layer, which can be used to facilitate coupling of the EOG electrode 30 to the scaffold 12 of the device 10, such as via sewing or with an adhesive.

In an example, the conductive structure 32 comprises one or more silver-coated threads 38, such as commercially available silver-coated nylon threads 38. In an example, a silver-coated nylon thread 38 that is used to form the conductive structure 32 has base resistivity of 2 kΩ/in or less. A silver-coated thread 38 provided for several advantages. First, the threads 38 have high conductivity, e.g., with the base resistivity being 2 kΩ/m or less. Second, the threads 38 have an acceptable mechanical tolerance and elongation, e.g., about ~24%, which results in the electrical properties changing by less than 10% under the application of all possible rubbing and stretching conditions that are expected to be experienced by the eye tracking device 10 (e.g., from about 0 to about 30% stretching). Third, using the silver-coated nylon threads 38 allows the electrode to be patterned into a specified shape. Fourth, the silver-coated threads 38 can be used with a variety of different fabrics and can be coupled relatively easily to the backing fabric layer 36 (as shown in the first step of fabricating the EOG electrode 30 shown in FIG. 4A). Fifth, the silver-coated threads 38 can also serve as the connection to the interconnect wiring 24 of the eye tracking device 10 (described in more detail below).

Finally, the silver coating of this conductive thread 38 makes it relatively easy and straightforward to manufacture the ionic interface material 44 on the conductive structure 32—which as noted above is necessary for signal transportation—through solution-based deposition. In an example, the ionic interface material 44 comprises a surface coating comprising an ionic interface material 44 on a specified portion 40 of the conductive structure 32 (also referred to hereinafter as the "ionic interface coating 44"). In the example wherein the conductive structure 32 comprises the silver-coated thread 38, the ionic interface coating 44 is formed by converting a portion of the silver metal coating the threading 38 to silver chloride (AgCl) such that the ionic interface coating 44 comprises an AgCl coating 44. In an example, the AgCl coating 44 is formed by applying a solution 42 of hypochlorite anions (ClO$^-$), for example a bleach solution 42, which comprises a solution of sodium hypochlorite (NaClO), to the specified portion 40 of the conductive thread 38, e.g., as shown in the second step of the example fabrication method shown in FIG. 4B. The bleach solution 42 reacts with the silver of the silver coated thread 38 to form the AgCl coating 44 of the conductive structure 32, e.g., as shown in the third step of the example fabrication method shown in FIG. 4C.

In an example, the backing fabric 36 of the electrode is treated so that it is hydrophobic to prevent the bleach solution 42 from leaking through the backing fabric 36 and reacting with parts of the silver-coated threads 38 other than the specified portion 40. In an example, the backing fabric 36 is made hydrophobic by pre-coating it with a hydrophobic coating, such as poly(heptadecafluorodecyl acrylate) ("pFDA"). In an example, the pFDA coating is applied to the backing fabric 36 using a solvent-free, vapor-phase deposition process called initiative chemical vapor deposition (iCVD). In an example, the silver-coated threads 38 were stitched into a rectangular-shaped array of as many as 50 silver-coated threads 38, or more, arranged on a small swatch of the backing fabric 36 (e.g., a 2 cm×3 cm, or 6 cm$^2$, switch) on top of which a thin, e.g., nanometers thick, layer of AgCl was created by reaction with bleach solution 42 to provide the AgCl-coated layer 44.

The textile-based hydrogel electrode 30 also includes a hydrogel body 46 in contact with the specified portion 40 of the conductive structure 32 that includes the ionic interface material (such as the AgCl-coated section 44 of the silver-coated threads 38 in the example described above). The hydrogel body 46 is in contact with the ionic interface material of the specified portion 40 of the conductive structure 32, e.g., by being in contact with the layer of AgCl of the AgCl-coated section 44 of the silver-coated threads 38, as shown in the fourth step of the example fabrication method in FIG. 4D. The hydrogel body 46 provides a wet material that can reduce the occurrence of unwanted motion artifacts. However, fabricating a hydrogel that can be stably coupled to the conductive textile structure of the EOG electrode 30 was found to be difficult. Even more difficult was the fabrication of a hydrogel material that can also be fully or nearly fully rehydrated after being dried out. In an example, the hydrogel body 46 was formed using initiative chemical vapor deposition. Initiative chemical vapor deposition (iCVD) is an efficient solution-free chain growth polymerization method that can produce highly conformal polymeric coatings on arbitrarily shaped substrates with different levels of roughness and/or porosity, such as on textiles. As used herein, the term "conformal" refers to a coating film that is relatively thin and matches or substantially matches the outer contours of the substrate onto which the film has been deposited.

In an example, the hydrogel material of the hydrogel body 46 comprises an electrolyte gel with a conductive material dispersed therein, such as conductive particles dispersed in the gel, for example silver particles dispersed in the gel. In an example, the electrolyte gel comprises a commercially-available silver gel, such as one that comprises water, polyacrylic acid (e.g., those sold under the tradename CARBOPOL by The Lubrizol Corp., Wickliffe, Ohio, USA), sodium bicarbonate ($NaHCO_3$), aloe vera, citric buffer, and silver. The silver in this example gel provides for both ionic conductivity through the gel and also has an antimicrobial effect.

Most gels such as the example silver gel have little to no mechanical stability and would be readily absorbed into the wearer's skin or rubbed away when the EOG electrode 30 came into contact with the wearer. Therefore, in an example, a stabilizing coating is applied onto the hydrogel body 46 to shield the gel from absorption and to provide the hydrogel body 46 with mechanical stability and reusability. In an example, the stabilizing coating comprises a poly-2-hydroxyethylacrylate ("pHEA") coating. Hydroxyethyl acrylates are biocompatible and are frequently used in biomedical and drug delivery. Fully polymerized hydroxyethyl acrylate is inert and proven to be harmless.

Figure 5:
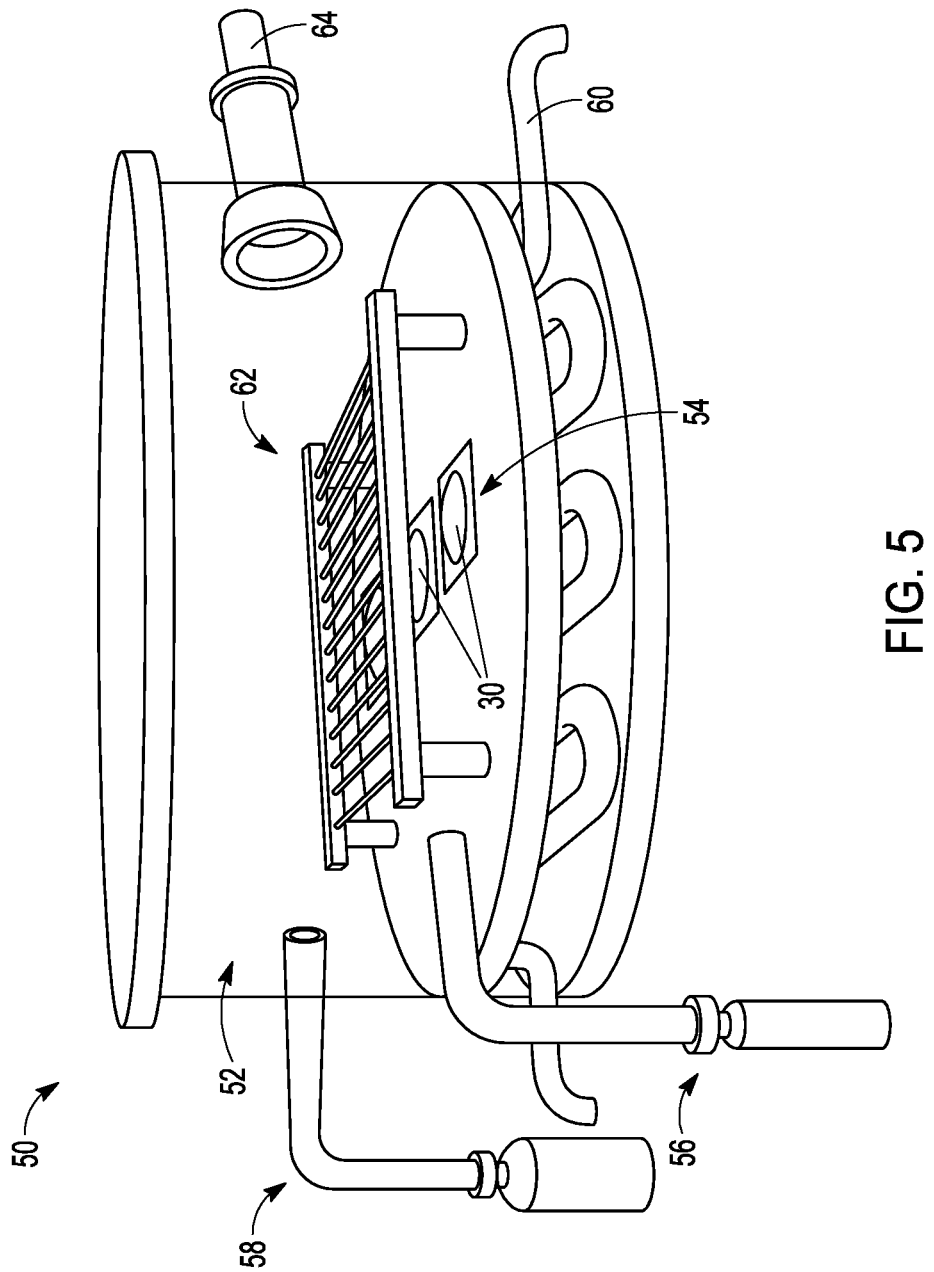
FIG. 5 is a perspective view of an example initiative chemical vapor deposition reactor for depositing a poly-2-hydroxyethylacrylate ("pHEA") stabilizing coating on a hydrogel body of the example textile-based hydrogel electrode of FIG. 3 or for depositing a poly(heptadecafluorodecyl acrylate) ("pFDA") hydrophobic coating on various structures of the example textile-based hydrogel electrode of FIG. 3, in accordance with various embodiments of the present disclosure.

In an example, the pHEA coating is formed by the polymerization of 2-hydroxyethylacrylate ("HEA") to form the pHEA, such as via iCVD, for example in the example iCVD reactor 50 shown in FIG. 5. As seen in FIG. 5, in an example, the iCVD reactor 50 includes a reactor chamber 52, a deposition stage 54 within the reactor chamber 52; a monomer feed 56; an initiator feed 58; a cooling apparatus 60, such as one or more cooling tubes 60, to control the temperature of the deposition stage 54; one or more heating structures 62, such as heating filaments 62, spaced from the deposition stage 54, which activate cleavage of an initiator compound (such as tert-butyl peroxide) to provide a reactive free radical species within the chamber 52. In an example, HEA is vaporized at 110° C. and introduced into the chamber 52 where it undergoes a chain polymerization reaction. The chain polymerization is initiated by the free radicals created by the cleavage of vaporized initiator, e.g., at about 300° C. for the tert-butyl peroxide initiator. In an example, the iCVD reactor 50 can also include a vacuum outlet 64 so that a vacuum may be applied to the reactor chamber 52.

Monomeric HEA can be irritants or allergens for some people if it is present as an impurity in the hydrogel body. Therefore, in some examples, the EOG electrode or electrodes 30 including the hydrogel body 46 are left in the iCVD reactor 50 for sufficient time such that the yield of the polymerization reaction is as close to 100% as possible. In some examples, the hydrogel body 46 is subjected to one or more purification operations to attempt to remove residual traces of unreacted HEA monomers that may be dissolved in the hydrogel matrix.

The super-hydrophilic nature of the pHEA coating, along with its polymerization from the vapor phase, leads to diffusion of the pHEA into the hydrogel material of the hydrogel body 46 (e.g., the silver gel material described above). Without wishing to be bound by any theory, the inventors believe that the diffused pHEA creates a cross-linked network comprising the hydrogel material and pHEA that is of sufficient density to provide mechanical stability for the hydrogel body 46. The cross-linked hydrogel network behaves mechanically similar to the foams being used in standard Ag/AgCl electrodes. This cushion-like nature of the hydrogel body 46 provides for little to no motion artifacts in the absence of any adhesives around.

The crosslinked network also allows the hydrogel body 46 to be wash-stable such that the textile-based hydrogel electrode 30 can be washed along with a fabric-based scaffold of the device 10. The crosslinked hydrogel network can also be allowed to dry out and then recovered with the addition of water so that the hydrogel body 46 can be rehydrated if and when it is needed.

Figure 6:
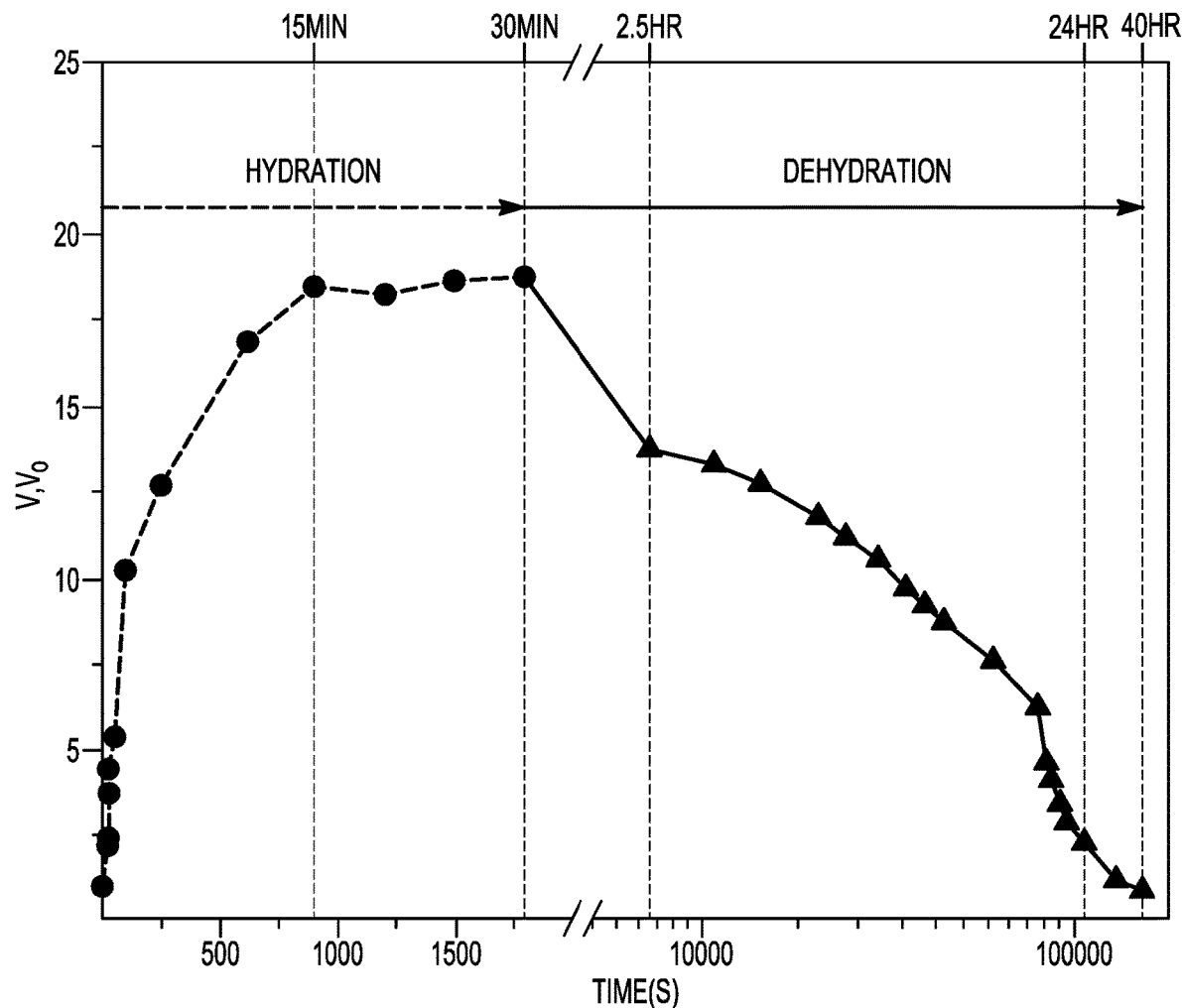
FIG. 6 is a graph showing a typical hydration-dehydration cycle for the hydrogel body of the example textile-based hydrogel electrode of FIG. 3, in accordance with various embodiments of the present disclosure.

The hydration and dehydration of the hydrogel body 46 described above was tested to evaluate the stability and reusability of the textile-based hydrogel electrode 30. Since the electrode 30 is designed to be hydrated frequently by users, and also because the electrode 30 is likely to come into contact with sweat, a swelling study was performed to determine the capacity of the hydrogel material for swelling when in contact with water and sweat. Three of the dry pHEA-coated hydrogel bodies 46 were immersed in water, and three were immersed in 10 millimolar (mM) sodium chloride (NaCl) solution until visually no observable change was detected in the degree of swelling of the samples. The dimensions of the swelled pHEA-hydrogel bodies 46 were measured using a caliper. The hydrogel bodies 46 were then allowed to dry in room temperature air with about 30% humidity for about 40 hours. The volume of each sample hydrogel body 46 was measured every hour during this drying process to get a general idea of the dehydration response time for the hydrogel material of the hydrogel body 46 when hydrated by water and sweat. After the 40 hours of drying, dehydration of the hydrogel material completed for both the water hydrated and NaCl solution hydrated hydrogel bodies 46, and all samples returned to their initial weight. FIG. 6 is a graph showing a typical hydration-dehydration cycle for one of the hydrogel bodies 46, with the change in volume shown in the vertical axis and the time elapsed in the horizontal axis. The response time for hydration/dehydration and associated volume changes shown in FIG. 6 remained essentially unchanged, even after 20 or more hydration/dehydration cycles. This hydration and dehydration study shows that the textile-based hydrogel electrodes 30 are highly robust for continued and repeated use.

In an example, the textile-based hydrogel electrode 30 includes a fabric-based framing layer 48 positioned on top of the stabilized hydrogel body 46. The framing layer 48 provides for a mechanically stable and conformable interface between the wearer's skin and the textile-based hydrogel electrode 30, while still allowing for direct contact between the hydrogel body 46 and the wearer's skin. The material of the framing layer 48 can be similar to the backing layer 36 on the bottom side of the conductive structure 32, described above. In an example, the framing layer 48 comprises a loose-weave cotton gauze on top, which protects the hydrogel body 46 from being delaminated and rubbed away while enabling hydration and direct contact with the wearer's skin. In an example, one or both of the yarn and fabric layers (e.g., the backing layer 36 and the framing layer 48) were coated with a hydrophobic coating to minimize or prevent water from absorbing into or onto the fabric layers 36, 48 rather than into the hydrogel body 46. In an example, one or both of the fabric-based layers 36, 48 were coated with a hydrophobic material, for example by fluoroalkylating the fabric with poly-perfluorodecylacrylate ("pFDA"), such as via iCVD of (1H, 1H, 2H, 2H-perfluorodecyl)acrylate ("FDA").

Figure 7:
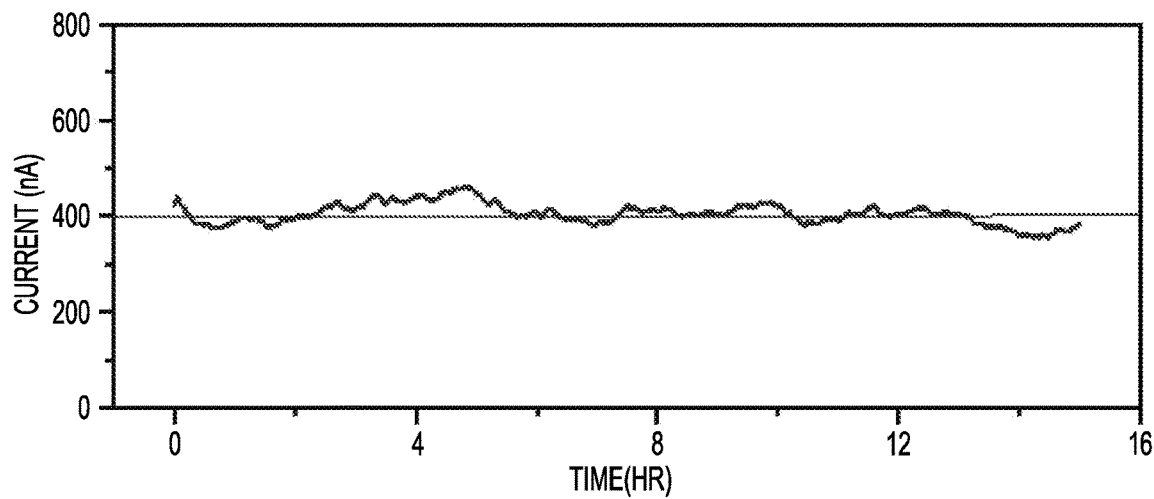
FIG. 7 is a chronoamperometry graph of the example textile-based hydrogel electrode of FIG. 3 over the course of sixteen (16) hours of continuous use, in accordance with various embodiments of the present disclosure.

Electrical properties of the textile-based hydrogel electrode 30 were tested to determine the longevity of the electrode 30 under the application of a constant voltage (e.g., about 0.25 mV) to evaluate the performance of the electrode 30 in biomedical applications, including eye tracking via EOG. As shown in FIG. 7, chronoamperometry of the electrode 30 revealed that the baseline electrical output of the electrode 30 remained unchanged after sixteen (16) hours of continuous use (e.g., continuous applied voltage) under ambient conditions. This result suggests that the electrodes 30 can be practically used for longitudinal eye tracking.

Figure 8:
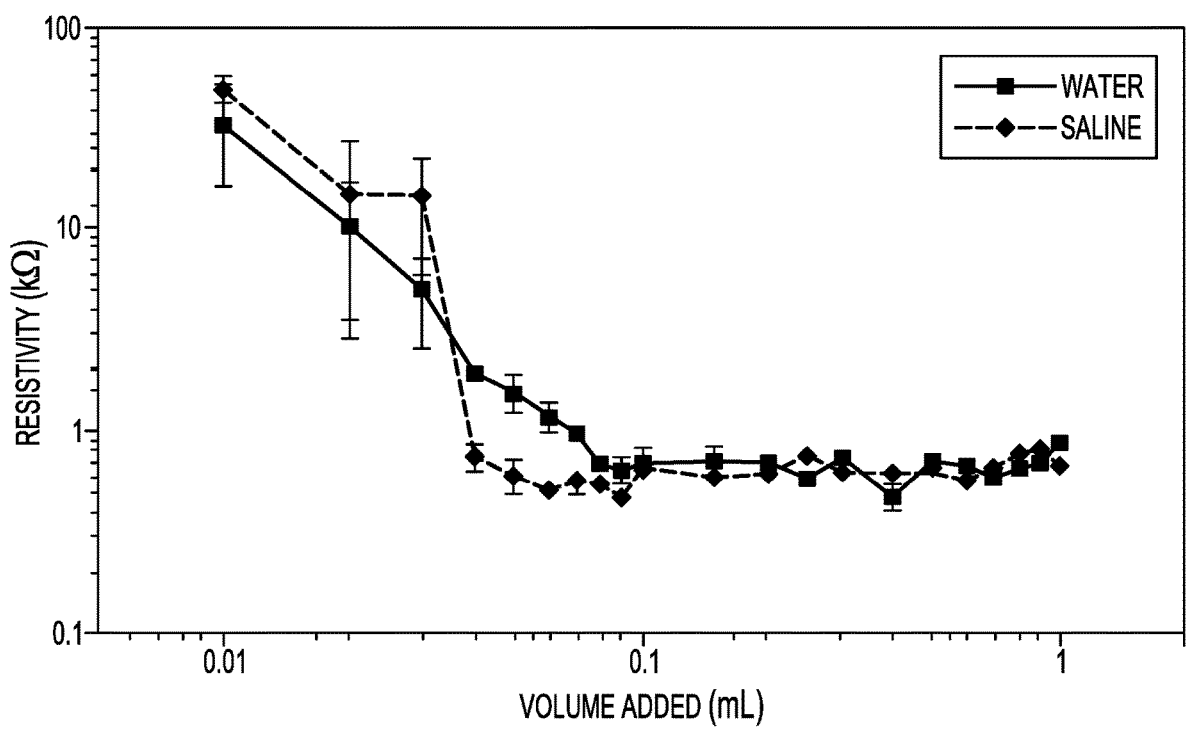
FIG. 8 is a graph showing change in resistivity as water or saline solution is added to the hydrogel body of the example textile-based hydrogel electrode of FIG. 3, in accordance with various embodiments of the present disclosure.

The effect of hydration and sweat on the resistivity of the textile-based hydrogel electrode 30 was also tested. FIG. 8 is a graph showing the change in resistivity of the electrode 30 as water or saline solution is added to the hydrogel body 46. As can be seen in FIG. 8, the resistivity drops with the very first droplet and remains almost constant with further addition of droplets. This suggests that the performance of the electrode 30 is essentially independent from the amount of hydration with water or sweat, which suggests that the textile-based hydrogel electrode 30 will be user-friendly for regular use in ordinary applications, including for video games, sleep monitoring, and other consumer applications.

Performance Testing of the Textile-Based Hydrogel Electrode

A plurality of the textile-based hydrogel electrodes 30 was incorporated into the eye mask scaffold 12, e.g., as the horizontal channel EOG electrodes 14A, the vertical channel EOG electrodes 14B, and the ground electrode 18 of the eye tracking device 10, as described above with respect to FIG. 2. Two control devices were also assembled, each using different conventional electrodes in place of the EOG electrode 30 of the present disclosure: The first control electrode was a conventional 3M wet electrode (referred to hereinafter as the "reference wet electrode"). The second control electrode was a silver-plated fabric electrode that acted as a dry electrode (referred to hereinafter as the "reference dry electrode"). The wearer wore the different eye masks at rest and moved her eyes along the horizontal and vertical line following a ball moving in a video with a fixed speed. The procedure was repeated for each of the three types of electrodes mounted on the eye mask.

Figure 9A:
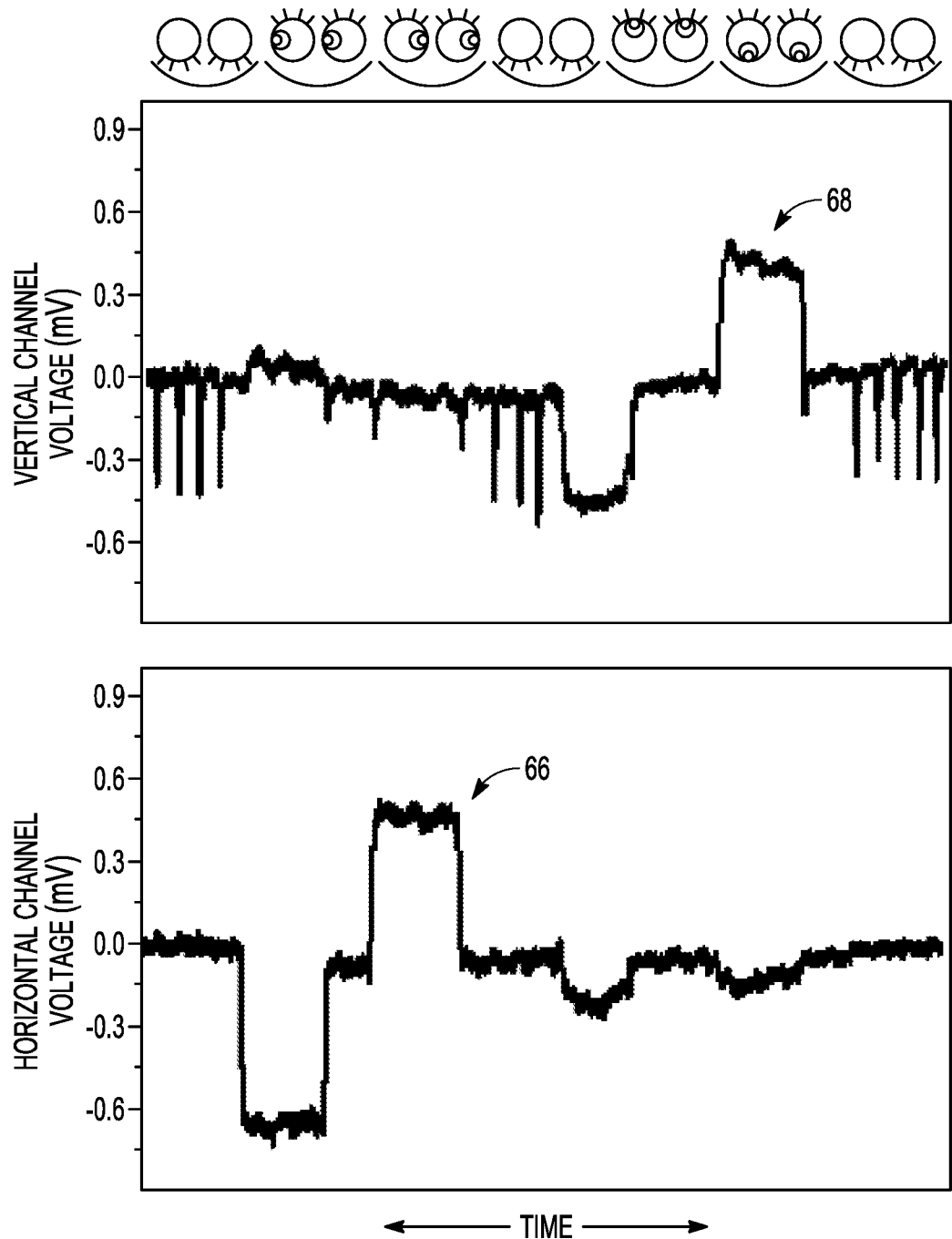
FIGS. 9A-9C shows the vertical channel and horizontal channel signals for the example textile-based hydrogel electrode of FIG. 3 compared to a conventional wet electrode and a dry silver-plated fabric electrode at the positions shown in FIG. 1 as a wearer's eyes moving to predetermined positions, in accordance with various embodiments of the present disclosure.
Figure 9B:
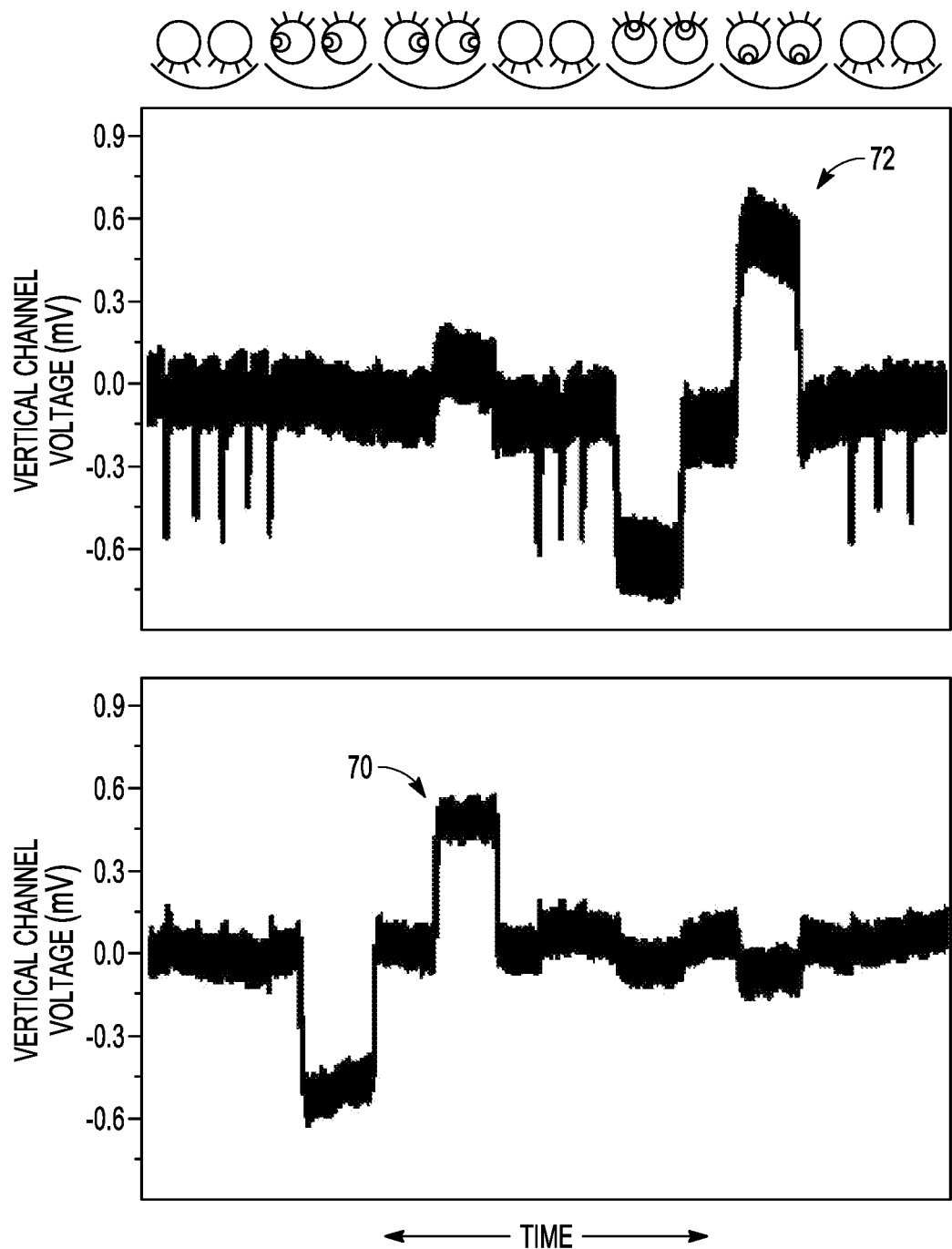
Figure 9C:
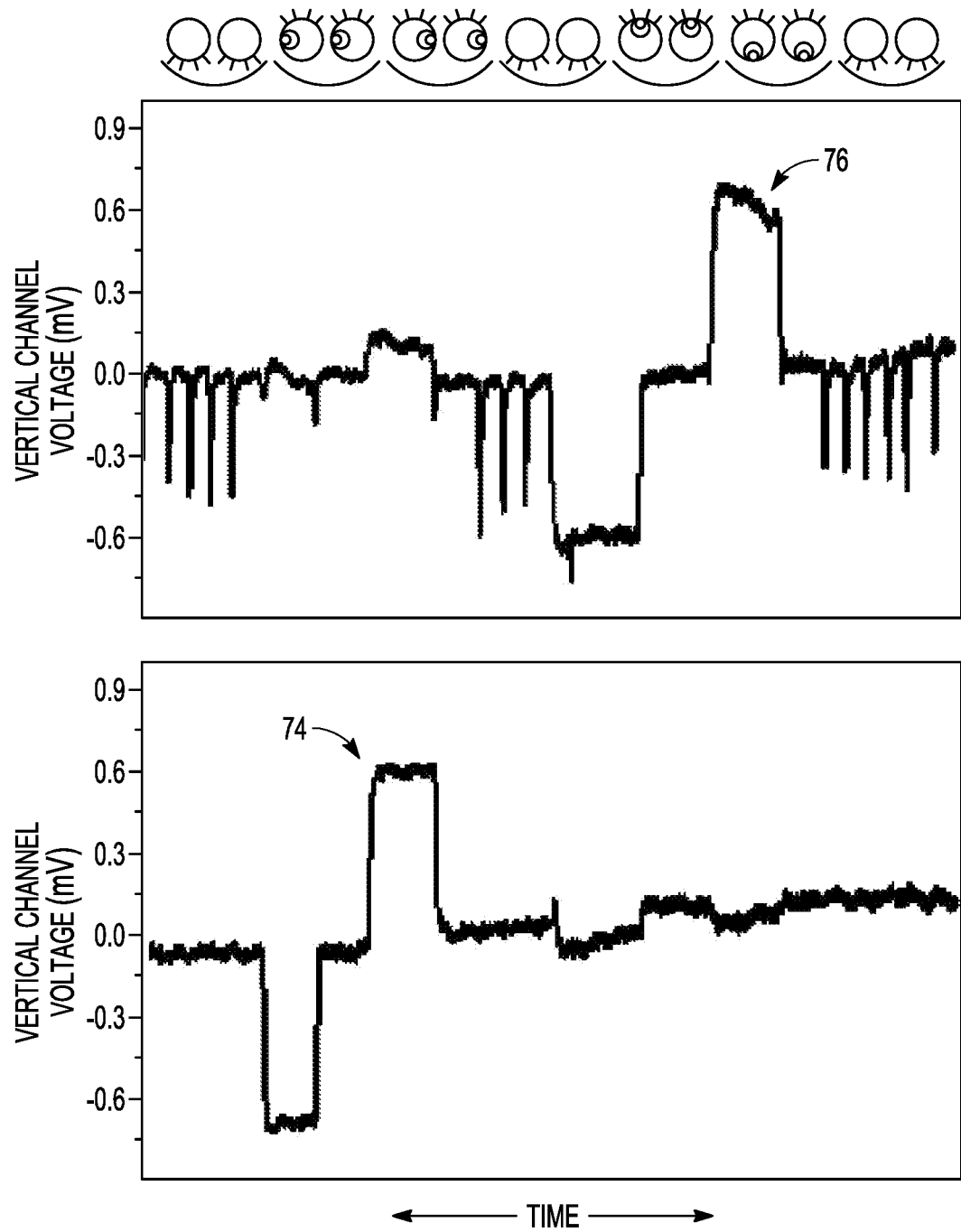

The vertical and horizontal EOG signals captured in these experiments are shown in FIGS. 9A-9C. FIG. 9A shows the signals from horizontal channel 66 and the vertical channel 68 from the EOG electrodes 30 of the present disclosure. FIG. 9B shows the signals from the horizontal channel 70 and the vertical channel 72 from the reference wet electrode. FIG. 9C shows the signals from the horizontal channel 74 and the vertical channel 76 from the reference dry electrode. As it can be seen, the horizontal channel signal 66 detected by the hydrogel-based EOG electrodes 30 of the present disclosure has almost the same strength as the horizontal channel signal 70 detected by the reference wet electrode, while the signal strength of the horizontal channel signal 74 of the reference dry electrode is less than the rest. In addition, both the horizontal and vertical channel signals 74, 76 of the reference dry electrode reveal a substantially noisier signal, while the hydrogel-based electrode 30 of the present disclosure was comparable to the noise of the reference wet electrode. These results suggest that the hydrogel-based electrodes 30 of the present disclosure are generally less susceptible to noise than dry electrodes.

Effect of Electrode-to-Skin Impedance Mismatch

As will be appreciated by those with skill in the art of bioelectrodes, a challenge to be addressed is the sizable impedance and unstable potential of bioelectrodes. Ideally, there would be zero potential or zero impedance at the points of contact between an electrode and the wearer's skin. Unfortunately, this ideal is not practically possible. One advantage of hydrogel or wet electrodes over dry electrodes is their surprisingly lower contact impedance. Generally, the difference between the two electrode potentials for the electrodes located on two opposing periorbital positions is amplified along with the amplification of the biosignal. However, almost always, there is not identical contact impedance between the two periorbitally-located electrodes (e.g., between the two horizontal channel electrodes 14A or between the two vertical channel electrodes 14B). In some situations, this difference in contact impedance can lead to a large mismatch in potentials (e.g., several hundreds of mV or more). When this occurs, it can be difficult or impossible to cancel out the potential difference with a differential amplifier, which results in saturation. The factors that may affect the mismatch in contact impedance include but are not limited to: the wearer's skin condition, which cannot be controlled by the eye tracking device and will tend to vary from person to person; and, the design of the EOG electrode 30, which, in certain examples can successfully overcome the contact impedance mismatch.

Figure 10:
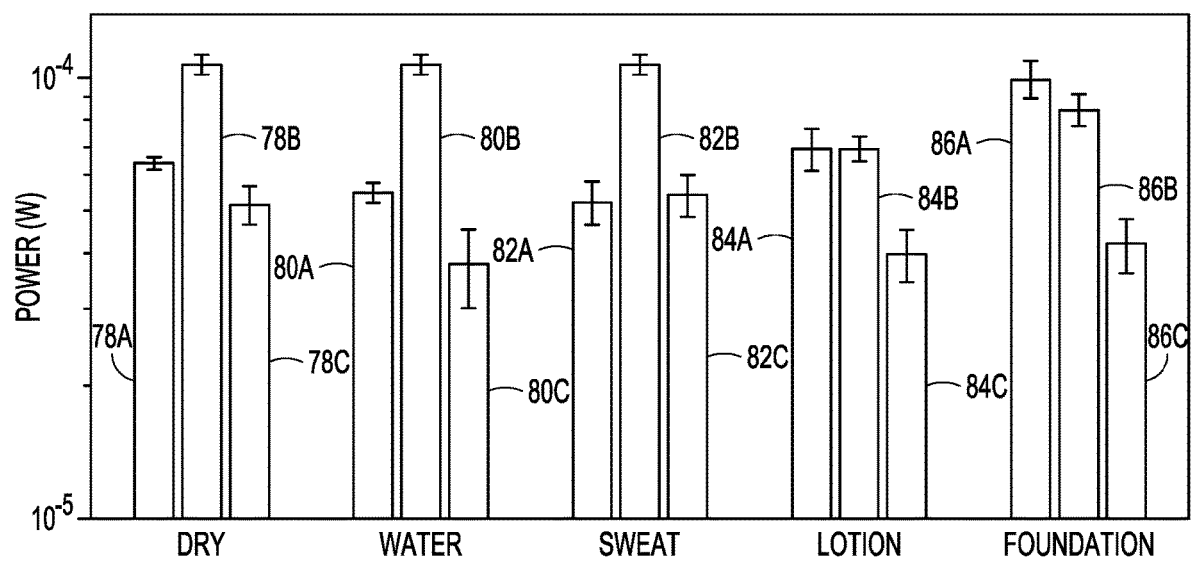
FIG. 10 is bar graph showing the signal amplitude of the example textile-based hydrogel electrode of FIG. 3, the conventional wet electrode, and the dry silver-plated fabric electrode for various skin conditions for the wearer, in accordance with various embodiments of the present disclosure.

In order to investigate the effect of wearer skin condition, the textile-based hydrogel electrode 30 was used to measure EOG signals for the wearer under five different skin conditions: dry bare skin, wetted with water, sweaty, with lotion applied, and with foundation makeup. FIG. 10 shows the resulting signal amplitude associated with measuring the EOG signal for each electrode type under each condition. In FIG. 10, data bars labeled with reference number 78 correspond to the dry bare skin condition, data bars labeled with reference number 80 correspond to the skin wetted with water, data bars labeled with reference number 82 correspond to the skin wetted with sweat, data bars labeled with reference number 84 correspond to skin with lotion applied, and data bars labeled with reference number 86 correspond to skin with foundation makeup applied. For each skin condition, reference numbers with a "A" designation (e.g., 78A for the dry skin condition) correspond to the textile-based hydrogel electrodes 30 of the present disclosure, those with a "B" designation (e.g., 82B for the "wetted with sweat" skin condition) correspond to the reference wet electrodes, and those with a "C" designation (e.g., 86C for the foundation makeup skin condition) correspond to the reference dry electrode. As can be seen in FIG. 10, the skin condition of the wearer had very little effect on the signal amplitude of the electrode 30 of the present disclosure, which is a promising sign for the mass production of the electrode.

Effect of Motion

One of the more important factors in the use of an electrode to measure biopotential, such as to measure eye movement via EOG or to measure brain electrical activity via EEG, is the effect of the wearer's movement and the development of so-called "motion artifacts" in the resulting recorded signal. Motion artifacts are the fluctuation in the signals coming from even the smallest movement by the wearer. One of the main sources of motion artifact is skin deformation that arises from a change in the thickness of the skin's epidermal layer due to stretching or compression of the skin. This change in thickness can directly affect a change in skin potential, which is the relative potential of the skin with respect to the inside of the body. It is for this reason that skin preparation can be incredibly important for commercial gel Ag/AgCl electrodes (e.g., shaving, applying alcohol to the skin to clean the area, and even abrading with sandpaper to exfoliate at least a portion of the dead layer skin). In addition, commercial gel electrodes, as well as dry (gel-less) electrodes, do not hydrate the skin, and, therefore, do not improve skin conductivity in long-term applications. Moreover, the signal degrades for commercial gel electrodes as the gel dries out, and the electrodes typically require reapplication of gel to the electrode or disposal and replacement of the electrode. However, as described above, the textile-based hydrogel electrode 30 of the present disclosure is designed so that the hydrogel body 46 can be relatively easily rehydrated before any application and will remain viable for up to at least about 48 hours. In addition, the inventors have found that in the example of the hydrogel body 46 formed with the silver gel hydrogel stabilized by the pHEA coating, described above, water will gradually soak into the wearer's skin during use, which renders the stratum corneum less resistive, resulting in the electrophysiological signal actually improving during long-term use of the textile-based hydrogel electrode 30 of the present disclosure.

Figure 11A:
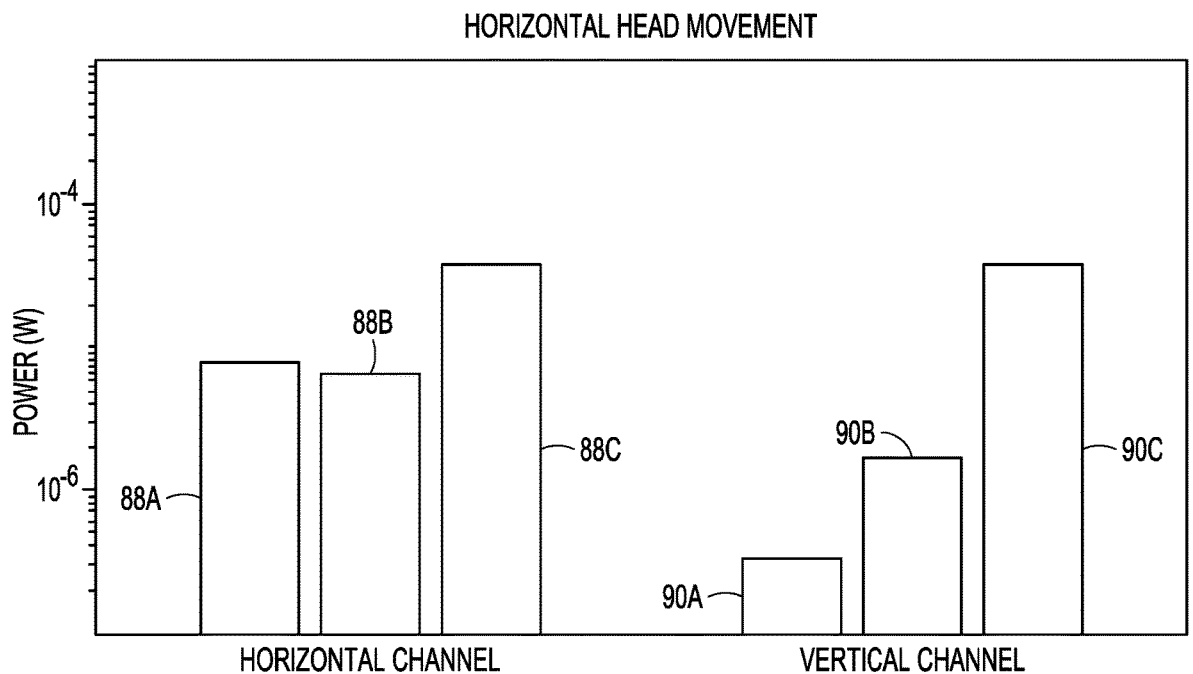
Figure 11B:
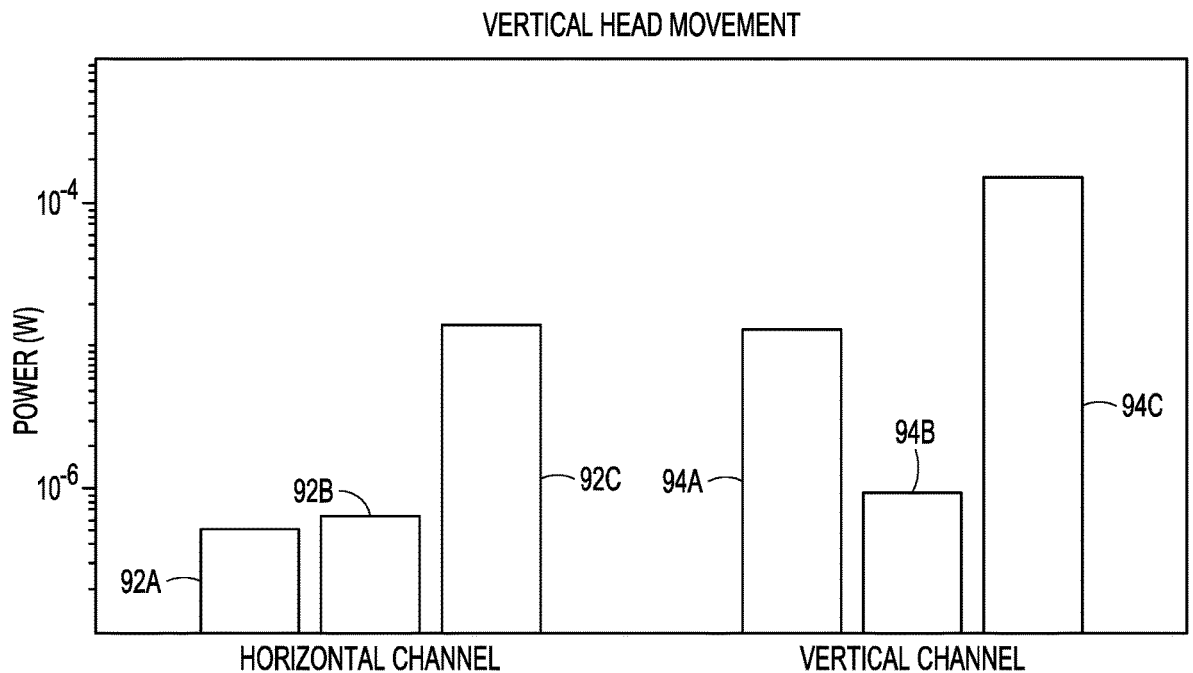
Figure 11C:
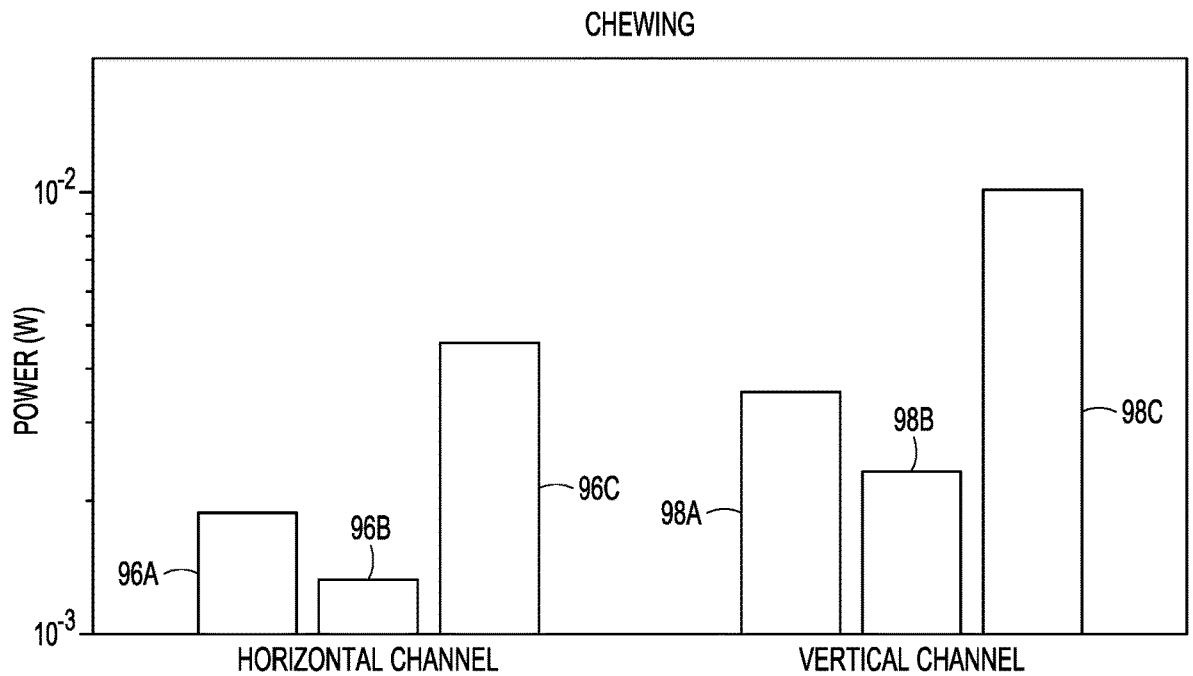
Figure 11D:
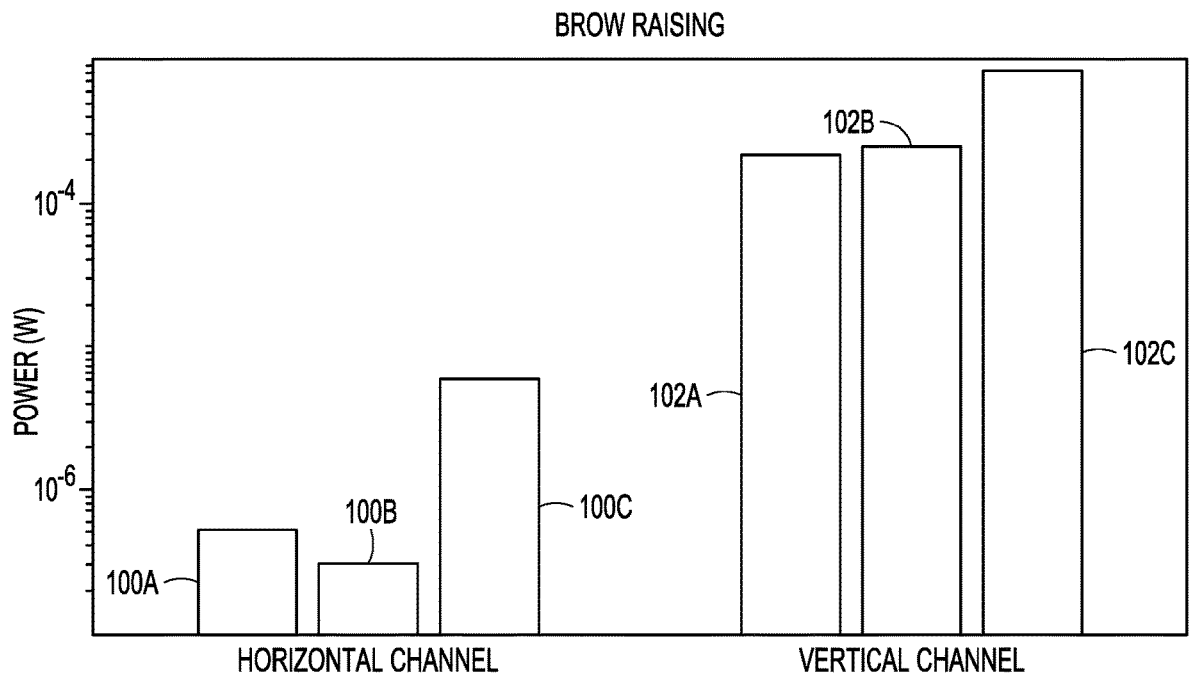

The effect of regular body movement and facial expressions on the electrophysiological signal was investigated by performing an EOG-based eye tracking test under four different conditions: horizontal head movement (e.g., rotation of the wearer's head), vertical head movement (e.g., flexion or extension of the neck upward and downward), chewing, raising the eyebrows, and talking (not shown). FIG. 11A shows the data for horizontal head movement, with data bars 88A, 88B, and 88C in FIG. 11A corresponding to the horizontal channel signals of the EOG electrode 30, the reference wet electrode, and the reference dry electrode, respectively, and data bars 90A, 90B, and 90C corresponding to the vertical channel signals of the EOG electrode 30, the reference wet electrode, and the reference dry electrode, respectively. FIG. 11B shows the data for vertical head movement, with data bars 92A, 92B, and 92C corresponding to the horizontal channel signals of the EOG electrode 30, the reference wet electrode, and the reference dry electrode, respectively and data bars 94A, 94B, and 94C corresponding to the vertical channel signals of the EOG electrode 30, the reference wet electrode, and the reference dry electrode, respectively. FIG. 11C shows the data for chewing, with data bars 96A, 96B, and 96C corresponding to the horizontal channel signals of the EOG electrode 30, the reference wet electrode, and the reference dry electrode, respectively, and data bars 98A, 98B, and 98C corresponding to the vertical channel signals of the EOG electrode 30, the reference wet electrode, and the reference dry electrode, respectively. Finally, FIG. 11D shows the data for brow raising, with data bars 100A, 100B, and 100C corresponding to the horizontal channel signals of the EOG electrode 30, the reference wet electrode, and the reference dry electrode, respectively, and data bars 102A, 102B, and 102C corresponding to the vertical channel signals of the EOG electrode 30, the reference wet electrode, and the reference dry electrode, respectively.

Figure 12A:
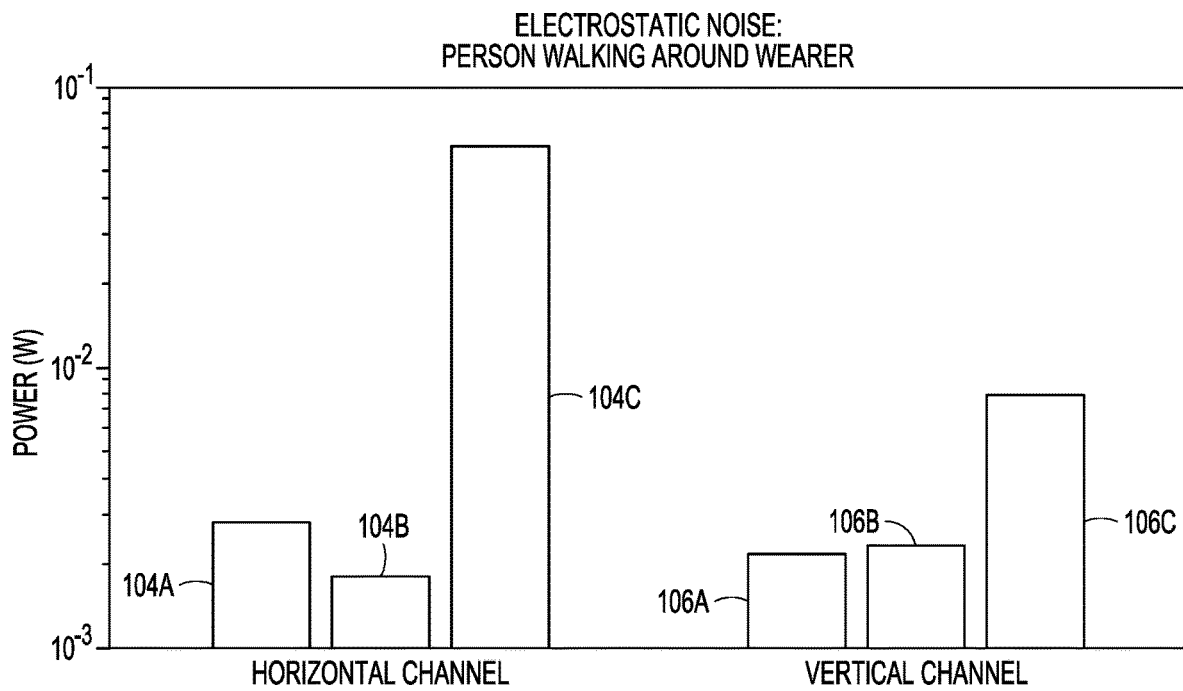
FIGS. 12A and 12B are bar graphs of the signal amplitudes of the example textile-based hydrogel electrode of FIG. 3, the conventional wet electrode, and the dry silver-plated fabric electrode when experiencing electrostatic noise and electromagnetic noise, respectively, in accordance with various embodiments of the present disclosure.
Figure 12B:
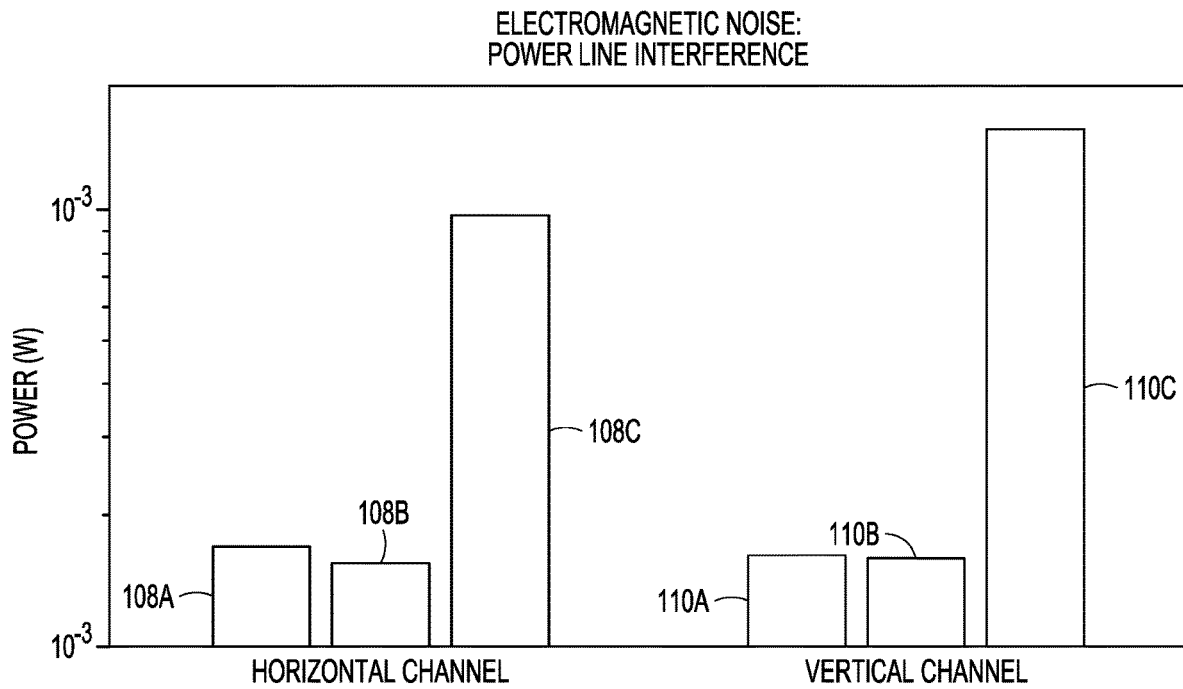

The effect of electrostatic noise was also investigated by having another person walk around the wearer while measuring eye movement via EOG, as was the effect of electromagnetic noise by investigating the effect of power line interference on the EOG signal measurement. FIG. 12A shows the data for the person walking around the wearer, with data bars 104A, 104B, and 104C corresponding to the horizontal channel signals of the EOG electrode 30, the reference wet electrode, and the reference dry electrode, respectively, and data bars 106A, 106B, and 106C corresponding to the vertical channel signals of the EOG electrode 30, the reference wet electrode, and the reference dry electrode, respectively. FIG. 12B shows the data for power line interference electromagnetic noise, with data bars 108A, 108B, and 108C corresponding to the horizontal channel signals of the EOG electrode 30, the reference wet electrode, and the reference dry electrode, respectively, and data bars 110A, 110B, and 110C corresponding to the vertical channel signals of the EOG electrode 30, the reference wet electrode, and the reference dry electrode, respectively.

Table 1 shows the signal-to-noise-ratio of each of the scenarios discussed with respect to FIGS. 11A-11D, 12A, and 12B as well as when the wearer is talking.

TABLE 1

Signal-to-Noise Ratio for Various Motion Artifacts and Noise Interference Scenarios

| | Electrode 30 | Reference Wet Electrode | Reference Dry Electrode |
|---|---|---|---|
| Talking | 12.81 | 2.17 | 18.90 |
| Chewing | 9.78 | 1.63 | 11.64 |
| Brow Raiser | −6.08 | −12.46 | −4.63 |
| Powerline | 18.31 | −2.62 | 21.04 |
| Passing Person | 14.11 | −16.43 | 16.31 |
| Horizontal Head Movement | 8.04 | −1.80 | 10.15 |
| Vertical Head Movement | 5.89 | −5.04 | 17.41 |

As shown in FIGS. 11A-11D and in Table 1, the effect of motion artifact in the textile-based hydrogel electrodes 30 of the present disclosure is comparable with or even less than in standard gel electrodes, and, as expected, dry electrodes give rise to the highest noise of all. The textile-based hydrogel electrodes of the present disclosure are also comparably affected by electrostatic noise and electromagnetic noise, as shown in FIGS. 12A and 12B and Table 1.

Pressure Sensor

As described above, in addition to the plurality of textile-based hydrogel electrodes 30 for registering a biopotential signal (e.g., for tracking eye movement via EOG), in an example the device 10 can include a pressure sensor 20 configured to measure the wearer's pulse during use of the device 10. As mentioned above, in an example, the pressure sensor 20 is positioned within the device 10 so that it is positioned in the approximate region of the wearer's supraorbital artery, as can be seen in FIGS. 1 and 2.

Figure 13:
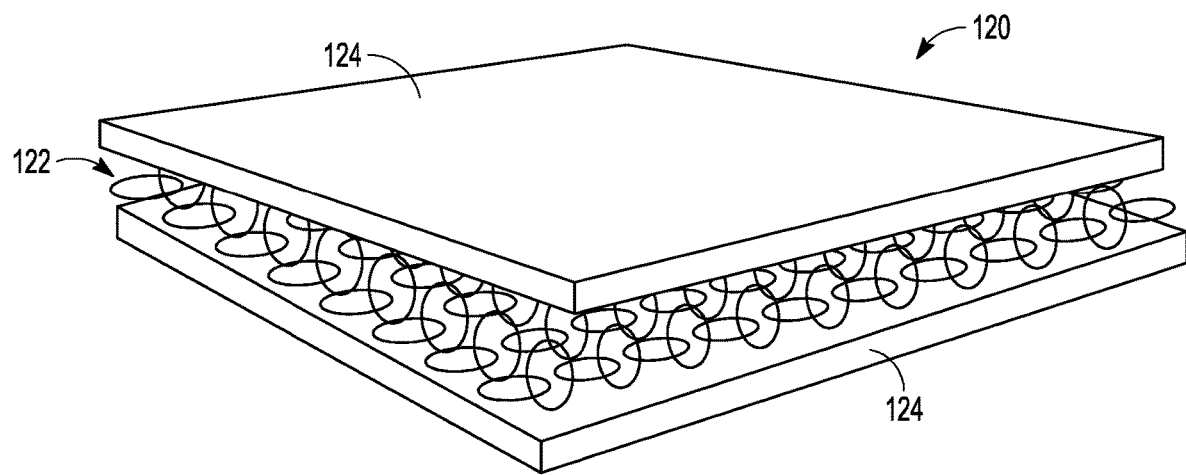
FIG. 13 is an exploded perspective view of an example pressure sensor for measuring a wearer's pulse, in accordance with various embodiments of the present disclosure.

FIG. 13 is schematic perspective view of an example pressure sensor 120 that can be used to measure the wearer's pulse, e.g., the example pressure sensor 120 of FIG. 13 can be used as the pressure sensor 20 for the eye tracking device 10 of FIG. 2. In an example, the measure of the wearer's pulse by the pressure sensor 120 can be performed simultaneously or substantially simultaneously with the tracking of the wearer's eyes via EOG, e.g., with a plurality of the EOG electrodes 30. The example pressure sensor 120 of FIG. 13 includes a fabric-based ion-conductive layer 122 sandwiched between a pair of fabric-based conductive layers 124. In an example, the outer conductive layers 124 each comprise a swatch of silver-coated fabric, such as a silver-coated nylon. Each conductive layer 124 acts as an electrode for the pressure sensor 120, while the middle ion-conductive layer 122 acts as the active layer of the pressure sensor 120. In an example, the middle ion-conducting layer 122 comprises a functionalized fabric layer, such as a functionalized cotton layer. In an example, the ion-conducting layer 122 comprises a porous, medium-density cotton fabric coated with a functionalizing compound, such as an alkoxy silane containing a positively charged quaternary ammonium moiety and chloride ion, as its counterion, which is biocompatible. In an example, the functionalized ion conductive layer 122 is encapsulated with perfluoroalkyl moieties through initiative chemical vapor deposition (iCVD). The hydrophobic nature of this coating provides the fabric of the ion-conducting layer 122 with a strong protective layer against aging processes such as washing or oxidation, so that the ionic conductivity in the fabric will not be washed away or diluted down if the wearer sweats while wearing the eye tracking device 10.

Figure 14:
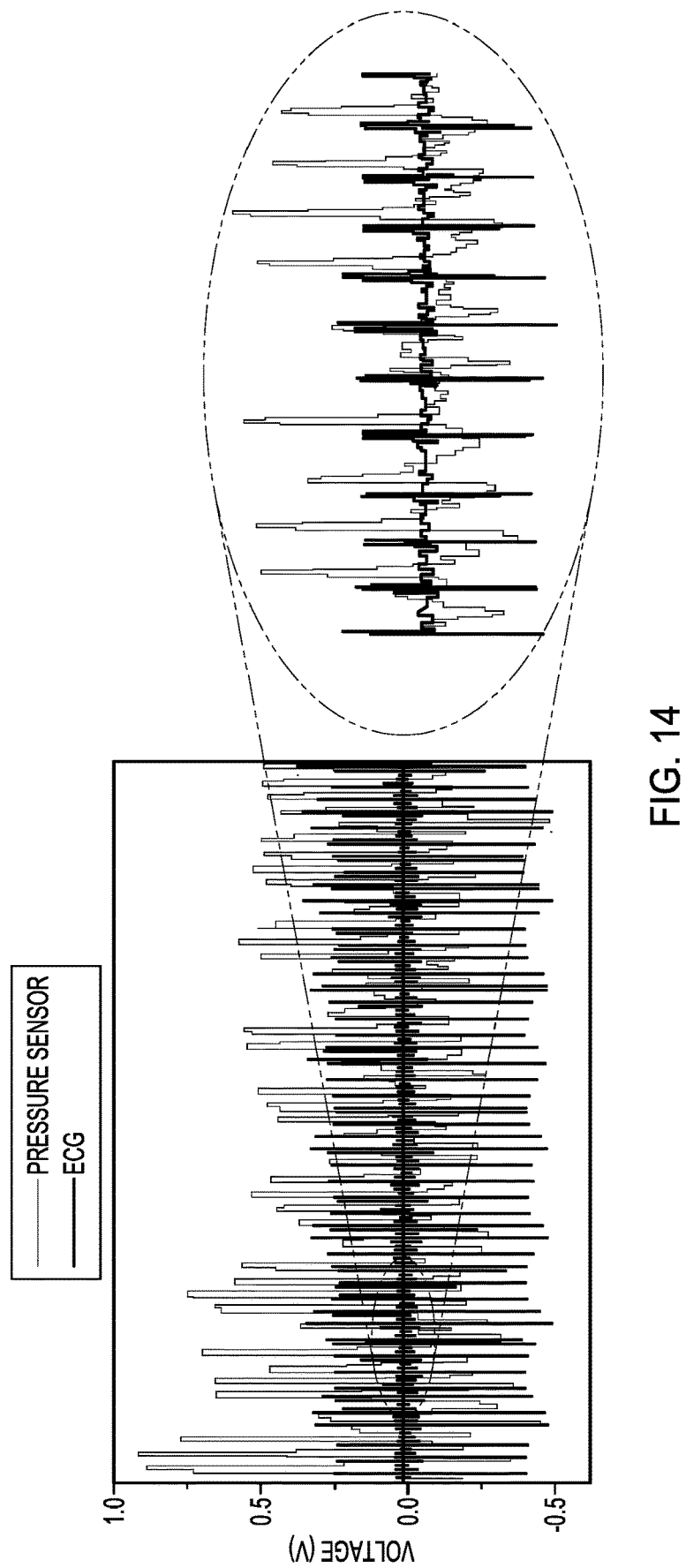
FIG. 14 is a graph of the signals acquired with the example pressure sensor of FIG. 13 located on a wearer's supraorbital artery position, which is confirmed with the electrocardiography signal measure simultaneously with commercial electrodes.

The mechanism of action of the pressure sensor 120 is an increase in the measured transverse conductivity of the pressure sensor 120 proportional to the pressure that is applied to the pressure sensor 120. The pressure exerted on the pressure sensor 120 by blood pulsing through the supraorbital artery was found to be sufficient to result in a clear signal output from the pressure sensor 120, as shown in FIG. 14. In order to confirm the validity of the data acquired through the pressure sensor 120, electrocardiography (ECG) was performed simultaneous with the measurement of the pressure sensor 120, which showed that the pressure sensor 120 is accurate when used as a pulse sensor.

Interconnect Wiring

The example textile-based hydrogel electrodes 14A, 14B, 18 and the example pressure sensor 20 can be electrically connected to other components of the wearable device 10, such as a controller 22 or a power source such as a battery 26. In an example, the eye tracking device 10 includes interconnect wiring 24 that is electrically connected to the textile-based hydrogel electrodes 14A, 14B, 18 and the pressure sensor 20, as well as other components of the eye tracking device 10, as shown in FIG. 2. In an example, the interconnect wiring 24 is formed from a conductive thread, which can be the same type of thread that can be used to form the conductive structure 32 of the textile-based hydrogel electrode 30 as described above, e.g., silver-coated threading, such as silver-coated nylon threads. Silver-coated threads such as these are useful in the wearable device 10 because they are highly conductive while still being flexible to accommodate motion of the eye tracking device 10 while it is worn. In an example, the conductive threading 24 is coated with a protective coating, such as a hydrophobic coating, for example a pFDA coating, to prevent the wiring 24 from shorting out and to protect the wiring from oxidation. The protective coating, such as a pFDA coating, can also provide wash stability for the wiring 24 while maintaining the electronic functionality of the eye tracking device 10. In an example, the conductive threads 24 are coated with pFDA via iCVD. In an example, the pFDA coated threads 24 are shielded inside cotton fabric, which can protect the threading 24 from electromagnetic fields and electrostatic noise.

Circuits and Communication Networks

There are several constraints on designing an amplification board for biopotential sensing applications, such as EOG or EEG, in the context of a wearable device. First, the amplitude of the signal from the textile-based hydrogel electrodes 14A, 14B, and 18, which results mainly from eye motion in the case of EOG or from brain activity in the case of EEG, can be on the order of tens of microvolts, which is well below the minimum detectable voltage swing for low power Analog to Digital Converters (ADC). Second, there is a varying DC baseline which depends on various physical conditions, such as electrode impedance matching, placement, and pressure on the wearer's skin surface. As a result of this varying DC baseline, the gain of the electronic circuit cannot exceed certain values to avoid voltage saturation at the output of the circuit board. This issue cannot be handled by DC-rejection methods, since the DC portion of the signal contains information regarding eyeball gaze direction. Third, the design is preferably low power and capable of fitting in a small form factor to facilitate mobility and comfort. In an example, the gain of the analog board was chosen so that the dynamic range of electrode impedance was preserved while obtaining information regarding measured biopotential, e.g., for tacking eye movement, even while using a low-power commercial ADC. In an example, the electronic design for each channel comprises a differential amplifier followed by filtering stages that mainly aim to reject power line noise. The amplified signal can be fed into the ADCs to be digitized and prepared for wireless transmission.

In an example, the signal intensity for the pressure sensor 20 was increased significantly in order to capture heartbeat pulses from the supraorbital artery. In an example, a second electronic board was included, wherein the second electronic board was configured to amplify the frequency components in the range of from about 2 Hz to about 10 Hz, which was found to cover the strongest components of heartbeat pulses. In an example, the second electronic board is connected to the pressure sensor 20 and amplifies the signal up to 400 times to capture tiny pressure changes due to the wearer's heartbeat. In an example, the second electronic board includes a unity-gain amplifier to isolate the pressure sensor 20 followed by a three-stage inverting active filter.

In an example, the wearable device 10 includes a wireless data device, such as a Bluetooth transmitter, which can allow for a comfortable user experience by transferring the data to nearby receivers using the wireless connection. A Bluetooth transmitter sends the digitized sensed signal to a receiver so that the data can be processed and, optionally plotted. In an example, a wireless connection was achieved with an off-the shelf Arduino esp32. An external 16-bit Adafruit ADS 1115 ADC was also used to reduce digitization noise.

Longitudinal Study

A longitudinal study of the effect of long-term use of the textile-based hydrogel electrodes 14A, 14B, 18 was conducted by comparing captured signal strength during continuous long-term wearing of the device 10 while using the textile-based hydrogel electrodes 14A, 14B, 18 to track eye movement via EOG. A participant was seated about 20 inches (about 50 cm) from a 22-inch monitor for 6 hours while wearing the device 10. To eliminate the effects of noises and the visual scene in the pattern of the eye movements and hence the signal strength, the wearer performed a simple eye movement every 30 minutes for a total of 13 iterations. During each iteration of the experiment, the participant was asked to remain stationary and follow a white ball moving on the black background of the monitor by just moving their eyes. Each experimental iteration included 20 vertical and 20 horizontal eye movements with the velocity of 22°/s and 28°/s and maximum distances of 15° and 26°, respectively. Each iteration took about 2 minutes and the participant was free to do anything after that, while wearing the device 10 including the textile-based hydrogel electrodes 14A, 14B, 18. The data was recorded via 16-bit ADC with a 160 Hz sampling rate, and after proper pre-processing, the power of the signal has been computed with the following formula:

$$\text{Signal Power} = \frac{1}{T}\sum_{t=0}^{T} x(t)^2$$

Figure 15:
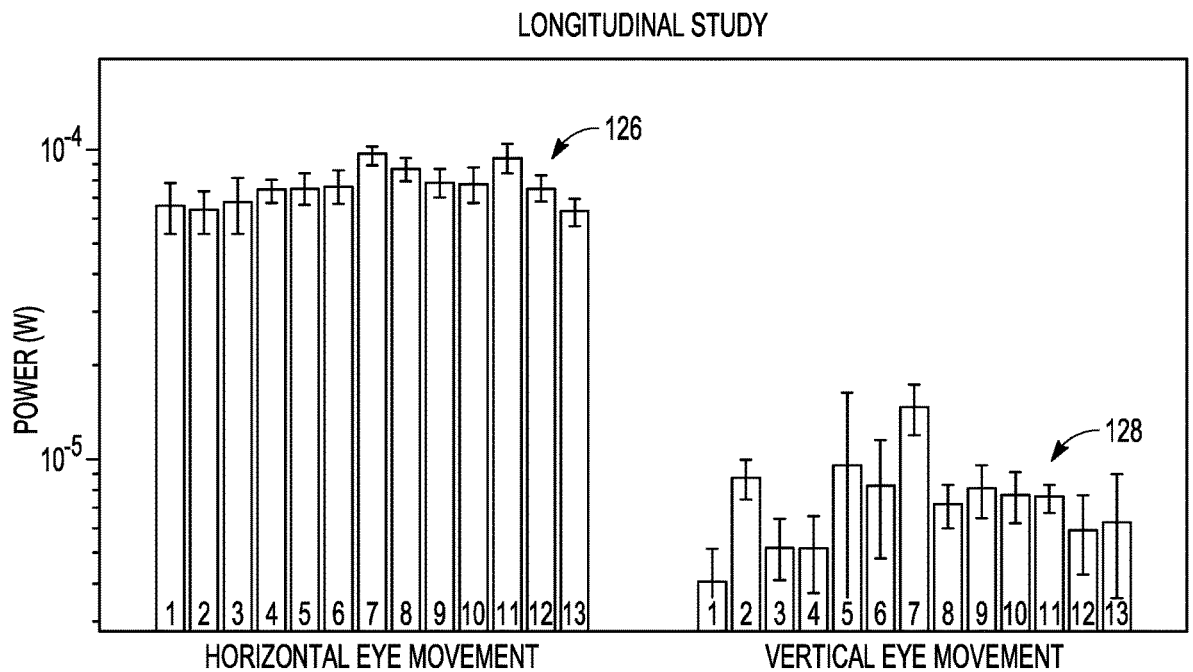
FIG. 15 is a bar graph of the signal strength for a longitudinal study of the example device of FIG. 2, in accordance with various embodiments of the present disclosure.

FIG. 15 shows the power data for each of the 13 iterations of the horizontal eye movements (data set 126, with each data bar labeled with the iteration number corresponding to that data) and the vertical eye movements (data set 128, with each data bar labeled with the iteration number corresponding to that data). As can be seen in FIG. 15, both the horizontal signals 126 and vertical signals 128 do not show much if any degradation, even after 6 hours of being continuously used by the wearer without any rehydration, which suggests the capability of the textile-based hydrogel electrodes to be used for long-term applications.

Figure 16:
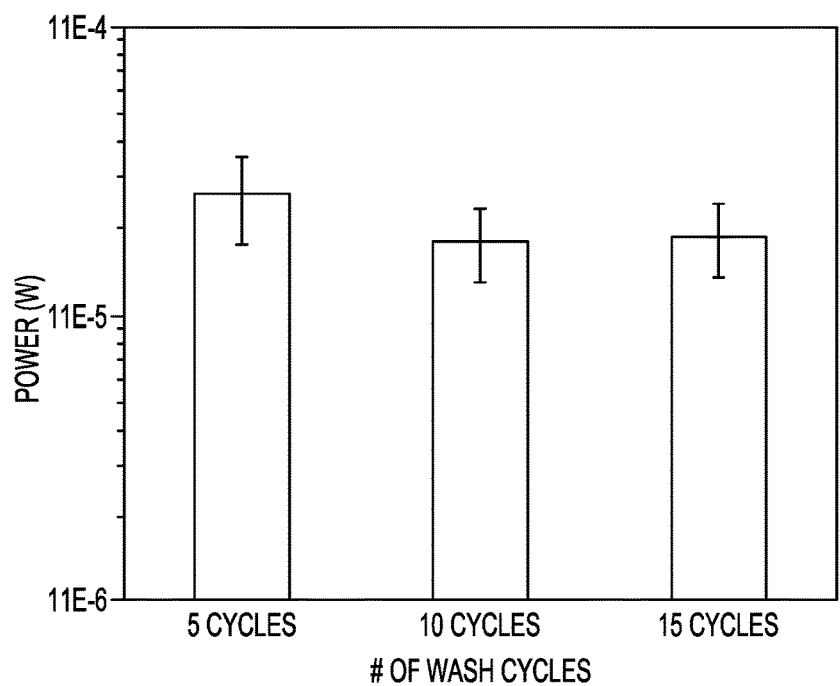
FIG. 16 is a bar graph of the signal amplitude of the example textile-based hydrogel electrode of FIG. 3 after zero (0) wash cycles, five (5) wash cycles, and ten (10) wash cycles, in accordance with various embodiments of the present disclosure.

In terms of wash-stability of the textile-based hydrogel electrodes, the electrical performance of the electrodes was studied by measuring the signal strength of EOG data with the textile-based hydrogel electrodes 14A, 14B, 18 after 5, 10 and 15 home laundering cycles. Each wash cycle included stirring the wearable device 10 at 300 rpm in a solution of water and laundry detergent (100/1 V/V) at 40° C., followed by rinsing with water for 10 min and drying at room temperature. As shown in FIG. 16, a very slight change is observed in the signal strength of the textile-based hydrogel electrodes 30 after being washed, which confirms that the textile-based hydrogel electrode of the present disclosure can withstand at least up to 15 home laundering operations.

Figure 17:
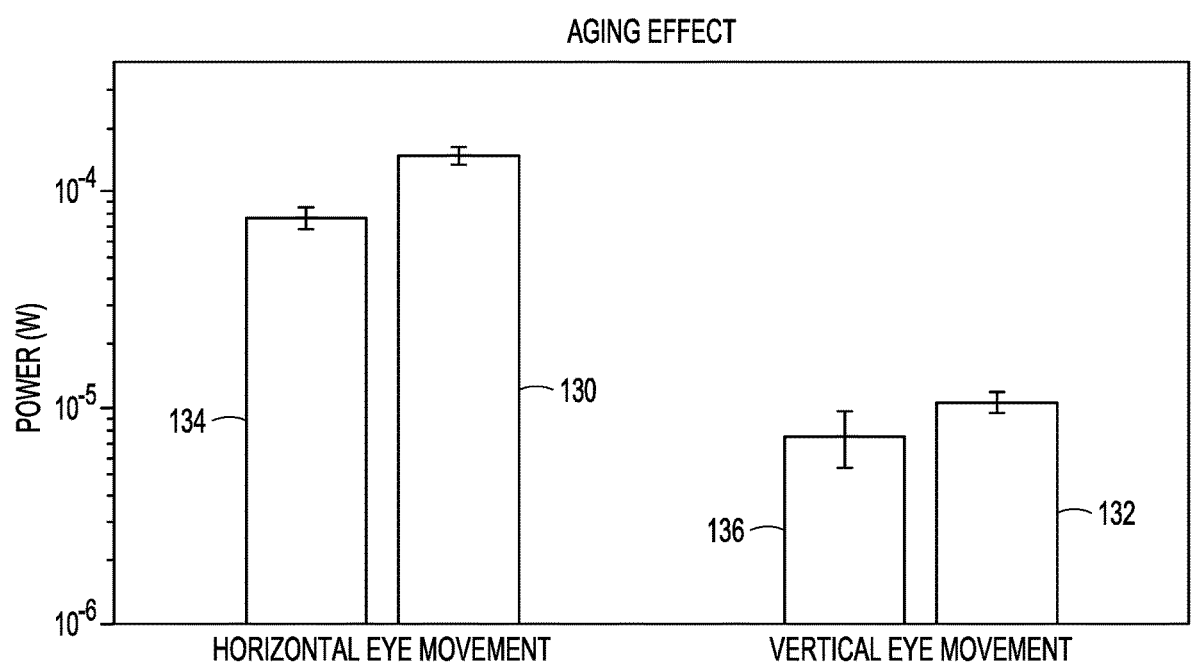
FIG. 17 is a bar graph of the aging effect on horizontal and vertical signal strength, for the example device of FIG. 2, in accordance with various embodiments of the present disclosure.

In addition to longitudinal study, it is desirable for a long-term health monitoring device, such as the wearable device 10, to be functional for a long period of time. Thus, the effect of aging on the textile-based hydrogel electrodes 30 was studied by measuring the eye movement signal from the same subject and with the same experimental setup after 6 months and 11 months. FIG. 17 shows data for the signal strength acquired from the horizontal channel textile-based hydrogel electrodes (e.g., electrodes 14A) and the vertical channel textile-based hydrogel electrodes (e.g., electrodes 14B) when the electrodes 14A, 14B are brand new (data bars 130 and 132, respectively) and when the electrodes 14A, 14B have been aged for 11 months (data bars 134 and 136, respectively). As can be seen in FIG. 17, both the horizontal channel electrodes 14A and the vertical channel electrodes 14B exhibit almost constant strength, with a very slight degradation after almost a year of use.

EXAMPLES

Various embodiments of the present invention can be better understood by reference to the following Examples which are offered by way of illustration. The present invention is not limited to the Examples given herein.

Example 1

Figure 4A:
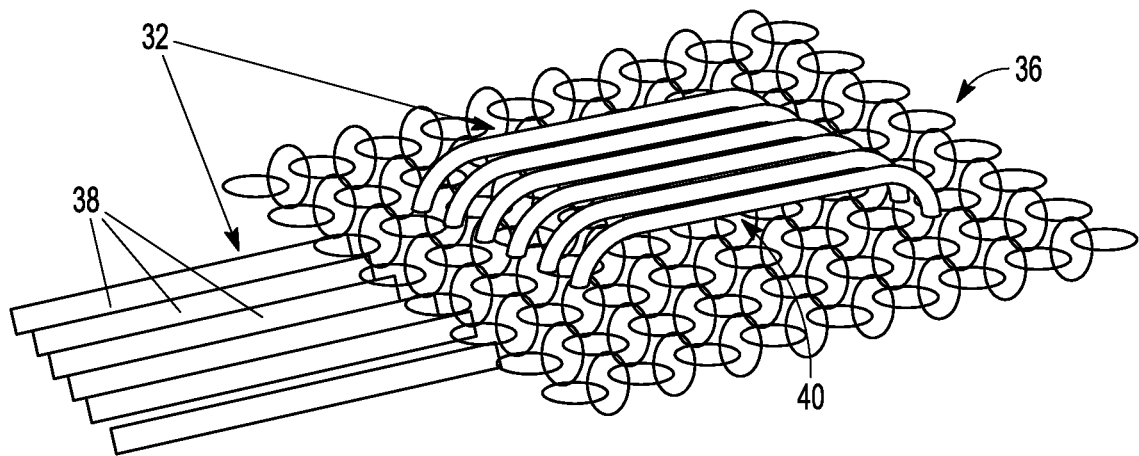
FIGS. 4A-4D are perspective views of several steps of an example method of fabricating the example textile-based hydrogel electrode of FIG. 3, in accordance with various embodiments of the present disclosure.
Figure 4B:
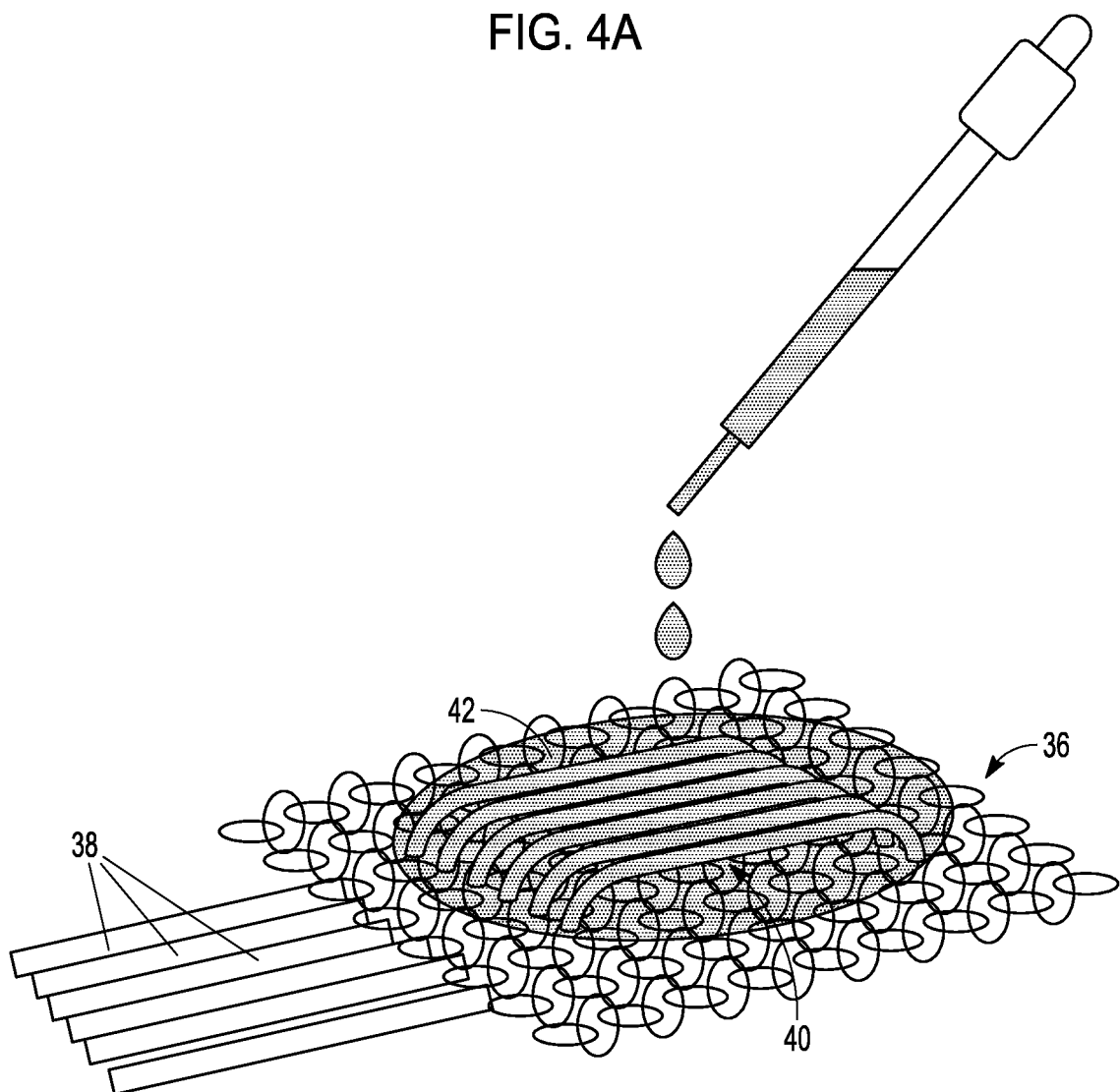
Figure 4C:
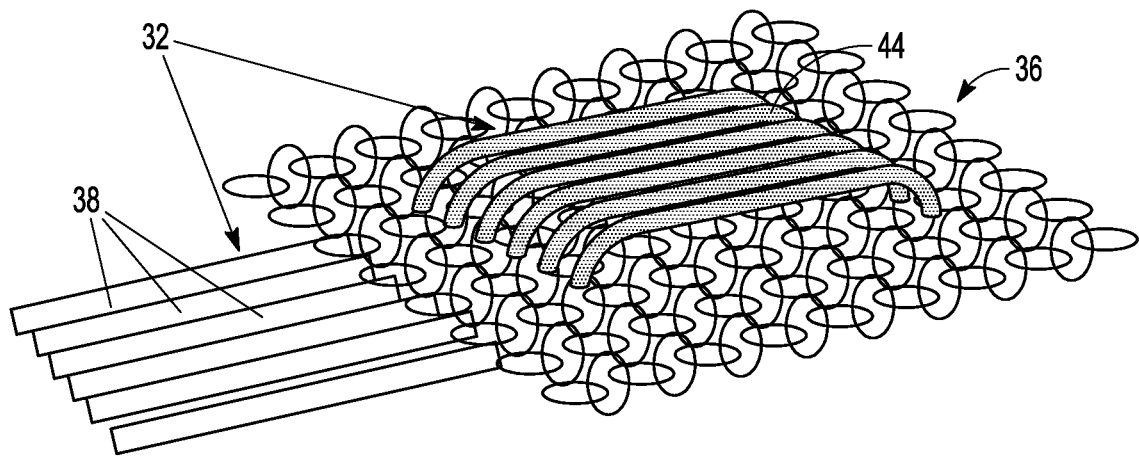
Figure 4D:
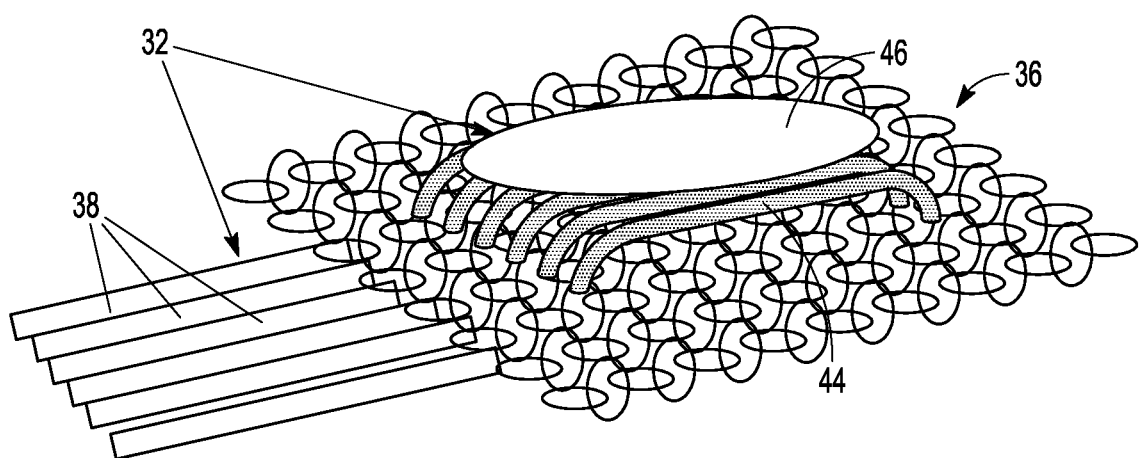

A sheet of cotton fabric was cut into several 2 cm×3 cm rectangular swatches, with each swatch forming the backing layer of one of the electrodes. Each swatch was sonicated in deionized water for 15 minutes and then rinsed with isopropanol and dried in air. On the center of each swatch, an array of approximately 50 silver-coated nylon threads (about 0.1 mm diameter, purchased form LessEMF) were stitched in a 1 cm×1.5 cm rectangular shape (see FIG. 4A). A solution of equal volumes laundry bleach (Clorox) and aqueous $AgNO_3$ (from Sigma Aldrich) was mixed in a beaker. 1 mL of the resulting bleach solution mixture was dropped onto the 1 cm×1.5 cm rectangular section of the silver thread in a way that covers the entire surface of the silver threads of the rectangular section (FIG. 4B). The silver threads were immersed in the bleach solution for approximately 40-50 seconds and then rinsed with deionized water and dried in the air. As a result, the portion of the silver threads in the 1 cm×1.5 cm rectangular section were coated with a thin layer of AgCl (see FIG. 4C).

About 0.4 mL of a commercial silver gel (comprised of water, CARBOPOL, sodium bicarbonate, sloe vera, citric buffer, and silver) was applied by doctor blade onto the rectangular portion of the thread that had been coated with AgCl. Then, the pre-applied gel samples were put inside the iCVD chamber (such as the example chamber 52 for the reactor 50 shown in FIG. 5) and coated with poly(hydroxyethyl acrylate) (pHEA). The iCVD process used 2-hydroxyethyl acrylate (HEA) as the monomer and tert-butyl peroxide (TBPO) (98%) as an initiator (both purchased from Sigma Aldrich and used without further purification). The 60-min deposition was conducted in a custom-designed cylindrical reactor (290 mm diameter, 70 mm height, FIG. 5) at a constant absolute pressure of about 1 Torr. The temperature of the filament was kept constant at 300° C., while the deposition stage was cooled and held at 15° C. After coating the silver gel with the pHEA, the resulting hydrogel body was stable and ready for use in an electrode (see FIG. 4D).

The electrode was encapsulated with poly(heptadecafluorodecyl acrylate) (pFDA) via iCVD of (1H, 1H, 2H, 2H-Perfluorodecyl)Acrylate (97%) as the monomer and tert-butyl peroxide (TBPO) (98%) as an initiator (both purchased from Sigma Aldrich and used without further purification). The 30-min deposition was conducted on the prewashed cotton gauze of the back layer and a cotton flannel of a framing layer as well as on the silver threads in the same iCVD chamber described above, at the constant pressure of 400 mTorr. All other conditions were the same as those used for the pHEA iCVD deposition.

EOG Electrode Chemical and Electrical Characterization

The surface component and valence state of the electrode was studied through X-ray Photoelectron Spectroscopy (XPS) (AXIS Ultra DLD). Stability of the electrode resistance over time was confirmed through three-electrode chronoamperometry by using a Wavenow potentiostat from Pine Instrument (results shown in FIG. 7). The resistivity of the hydrogel was studied using a four-point-probe measurement station equipped with an SP4 probe (Pro4-440N, Lucas Labs) (results shown in FIG. 8). The radius of tungsten-carbide tips was 0.04 mm and the relative distance between them was 1.27 mm.

Electrode Cytotoxicity Test

The cytotoxicity of the produced pHEA-hydrogel and pFDA was assessed in vitro on a culture of mouse fibroblast cells (standard L-929) (ATCC CCL-1). The test was carried out by Nelson Laboratories (Salt Lake City, Utah, USA) in accordance with criteria established by US Pharmacopeia and National Formulary (USP 87) and the ANSI/AAMI/ISO 10993-5 standards. The cytotoxicity test found no toxicity.

Electrode Viability in Other Applications: Electrocardiography

In order to confirm electrode functionality in other health monitoring applications such as electrocardiography, a commercial three-lead health monitoring device (Prince 180B from Heal Force) measured ECG through the electrodes of EXAMPLE 1. The signal produced by the textile-based hydrogel electrodes of EXAMPLE 1 and from commercially available "Red Dot™" brand electrodes (3M, St. Paul, MN, USA) are shown in FIGS. 18A and 18B, respectively. This observation suggests that these electrodes can be a viable option to be used in health monitoring applications.

Example 2

A pressure sensor was formed as a 25 mm×25 mm patch formed from two layers of a silver-plated nylon fabric holding two layers of ion conductive functionalized cotton gauze therebetween. The functionalized layers were fabricated by first sonicating a cotton gauze in deionized water for 15 min followed by rinsing with isopropanol. The cotton gauze was then soaked in N-trimethoxysilylpropyl-N,N,N, trimethylammonium chloride/isopropanol (15/100 V/V) for 30 min, followed by 2 hours of curing at 100° C. Then, the chemically grafted fabric was rinsed with isopropanol and dried in the air over night. In order to provide the sensor with wash-stability and durability, a vapor deposition of trichloro-(1H, 1H, 2H, 2H-perfluorooctyl)silane was performed via the same method as described in EXAMPLE 1. This deposition was performed at the constant pressure of 1 Torr for 30 minutes. The functionalized layers of cotton gauze were then cut into two 25 mm×25 mm swatches. Each of the two functionalized cotton gauze swatches was sewn onto a 20 mm×20 mm sheet of silver coated nylon to form a bilayer sheet. The final four-layer pressure sensor was produced by sewing these two bilayer sheets together around the perimeter with the functionalized cotton gauze sides facing toward each other.

To better illustrate the apparatuses and methods disclosed herein, a non-limiting list of exemplary EMBODIMENTS is provided here:

EMBODIMENT 1 can include subject matter (such as an apparatus, a device, a method, or one or more means for performing acts), such as can include a textile-based hydrogel electrode comprising a textile-based backing layer, a conductive structure coupled to the textile-based backing layer, and a hydrogel body in contact with at least a first portion of the conductive structure, wherein the first portion of the conductive structure and the hydrogel body form an ionic interface that generates an electrical signal through the conductive structure corresponding to a biopotential change proximate to the textile-based hydrogel electrode.

EMBODIMENT 2 can include or can optionally be combined with the subject matter of EMBODIMENT 1, to optionally include the first portion of the conductive structure comprising silver metal.

EMBODIMENT 3 can include or can optionally be combined with the subject matter of one or any combination of EMBODIMENTS 1 and 2, to optionally include the first portion of the conductive structure comprising silver chloride.

EMBODIMENT 4 can include or can optionally be combined with the subject matter of one or any combination of EMBODIMENTS 1-3, to optionally include the first portion of the conductive structure comprising a silver chloride coating portion of silver metal.

EMBODIMENT 5 can include or can optionally be combined with the subject matter of one or any combination of EMBODIMENTS 1-4, to optionally include the conductive structure comprising one or more metal-coated threads.

EMBODIMENT 6 can include or can optionally be combined with the subject matter of one or any combination of EMBODIMENTS 1-5, to optionally include the conductive structure comprising one or more silver-coated threads.

EMBODIMENT 7 can include or can optionally be combined with the subject matter of one or any combination of EMBODIMENTS 1-6, to optionally include the hydrogel body comprising a water-based gel with electrically conductive particles dispersed therein.

EMBODIMENT 8 can include or can optionally be combined with the subject matter of one or any combination of EMBODIMENTS 1-7, to optionally include a stabilizing coating applied onto the hydrogel body.

EMBODIMENT 9 can include or can optionally be combined with the subject matter of EMBODIMENT 8, to optionally include the stabilizing coating comprising poly-2-hydroxyethylacrylate.

EMBODIMENT 10 can include or can optionally be combined with the subject matter of one or any combination of EMBODIMENTS 8 or 9, to optionally include the stabilizing coating comprising a coating material that forms a crosslinked network with a hydrogel material of the hydrogel body.

EMBODIMENT 11 can include or can optionally be combined with the subject matter of one or any combination of EMBODIMENTS 1-10, to optionally include the hydrogel body being wash stable.

EMBODIMENT 12 can include or can optionally be combined with the subject matter of one or any combination of EMBODIMENTS 1-11, to optionally include the hydrogel body being dehydratable and rehydratable.

EMBODIMENT 13 can include or can optionally be combined with the subject matter of one or any combination of EMBODIMENTS 1-12, to optionally include a framing layer in contact with the hydrogel body opposite the conductive structure.

EMBODIMENT 14 can include or can optionally be combined with the subject matter of one or any combination of EMBODIMENTS 1-13, to optionally include the electrical signal comprising at least one of: an electrooculogram corresponding to a corneo-retinal standing potential of an eye; an electroencephalogram corresponding to neurological electrical activity; an electrocardiogram corresponding to cardiac electrical activity; and an electromyogram corresponding to electrical activity of one or more muscles.

EMBODIMENT 15 can include, or can optionally be combined with the subject matter of one or any combination of EMBODIMENTS 1-14, to include subject matter (such as an apparatus, a device, a method, or one or more means for performing acts), such as can include a method of manufacturing a textile-based hydrogel electrode, the method comprising the steps of coupling a conductive structure to a textile-based backing layer, and depositing a hydrogel material onto the conductive structure to form a hydrogel body that is in contact with a specified portion of the conductive structure, wherein the specified portion of the conductive structure comprises a first material that ionically interacts with the hydrogel material to form an ionic interface between the hydrogel body and the conductive structure, and wherein the ionic interface is configured to generate an electrical signal through the conductive structure corresponding to a biopotential change proximate to the ionic interface.

EMBODIMENT 16 can include or can optionally be combined with the subject matter of EMBODIMENT 15, to optionally include chemically modifying the specified portion of the conductive structure to provide the first material.

EMBODIMENT 17 can include or can optionally be combined with the subject matter of one or any combination of EMBODIMENTS 15 and 16, to optionally include at least the specified portion of the conductive structure comprising silver metal.

EMBODIMENT 18 can include or can optionally be combined with the subject matter of EMBODIMENT 17, to optionally include chemically converting at least a portion of the silver metal to silver chloride (AgCl).

EMBODIMENT 19 can include or can optionally be combined with the subject matter of EMBODIMENT 18, to optionally include contacting at least the portion of the silver metal with a solution comprising hypochlorite ions ($OCl^-$).

EMBODIMENT 20 can include or can optionally be combined with the subject matter of one or any combination of EMBODIMENTS 15-19, to optionally include the hydrogel material comprising a water-based gel with electrically conductive particles dispersed therein.

EMBODIMENT 21 can include or can optionally be combined with the subject matter of one or any combination of EMBODIMENTS 15-20, to optionally include applying a stabilizing coating to at least a portion of the hydrogel body.

EMBODIMENT 22 can include or can optionally be combined with the subject matter of EMBODIMENT 21, to optionally include the stabilizing coating comprising poly-2-hydroxyethylacrylate.

EMBODIMENT 23 can include or can optionally be combined with the subject matter of one or any combination of EMBODIMENTS 21 and 22, to optionally include the stabilizing coating comprising a coating material that forms a crosslinked network with the hydrogel material of the hydrogel body.

EMBODIMENT 24 can include or can optionally be combined with the subject matter of one or any combination of EMBODIMENTS 15-23, to optionally include the hydrogel body being wash stable.

EMBODIMENT 25 can include or can optionally be combined with the subject matter of one or any combination of EMBODIMENTS 15-24, to optionally include the hydrogel body being dehydratable and rehydratable.

EMBODIMENT 26 can include or can optionally be combined with the subject matter of one or any combination of EMBODIMENTS 15-25, to optionally include hydrophobically treating the textile-based backing layer.

EMBODIMENT 27 can include or can optionally be combined with the subject matter of one or any combination of EMBODIMENTS 15-26, to optionally include applying a hydrophobic coating to the textile-based backing layer.

EMBODIMENT 28 can include or can optionally be combined with the subject matter of one or any combination of EMBODIMENTS 15-27, to optionally include coupling a textile-based framing layer to the textile-based backing layer so that at least a portion of the framing layer is in contact with the hydrogel body opposite the conductive structure.

EMBODIMENT 29 can include or can optionally be combined with the subject matter of EMBODIMENT 28, to optionally include hydrophobically treating the textile-based framing layer.

EMBODIMENT 30 can include or can optionally be combined with the subject matter of one or any combination of EMBODIMENTS 28 and 29, to optionally include applying a hydrophobic coating to the textile-based framing layer.

EMBODIMENT 31 can include or can optionally be combined with the subject matter of one or any combination of EMBODIMENTS 15-30, to optionally include the electrical signal comprising at least one of: an electrooculogram corresponding to a corneo-retinal standing potential of an eye; an electroencephalogram corresponding to neurological electrical activity; an electrocardiogram corresponding to cardiac electrical activity; and an electromyogram corresponding to electrical activity of one or more muscles.

EMBODIMENT 32 can include, or can optionally be combined with the subject matter of one or any combination of EMBODIMENTS 1-31, to include subject matter (such as an apparatus, a device, a method, or one or more means for performing acts), such as can include a wearable biopotential measuring device comprising a support scaffold configured for wearing by a subject, and a plurality of textile-based hydrogel electrodes coupled to the scaffold so that when the support scaffold is worn by the subject, each of the plurality of textile-based hydrogel electrodes are positioned proximate to a corresponding specified bodily structure of the subject, wherein each of the plurality of textile-based hydrogel electrodes is configured to generate an electrical signal corresponding to a biopotential change of the corresponding specified bodily structure.

EMBODIMENT 33 can include or can optionally be combined with the subject matter of EMBODIMENT 32, to optionally include at least one of the textile-based hydrogel electrodes comprising a textile-based backing layer, a conductive structure coupled to the textile-based backing layer, and a hydrogel body in contact with at least a first portion of the conductive structure, wherein the first portion of the conductive structure and the hydrogel body form an ionic interface that generates the electrical signal corresponding to the biopotential change of the corresponding specified bodily structure.

EMBODIMENT 34 can include or can optionally be combined with the subject matter of EMBODIMENT 33, to optionally include the first portion of the conductive structure comprising silver metal.

EMBODIMENT 35 can include or can optionally be combined with the subject matter of one or any combination of EMBODIMENTS 33 and 34, to optionally include the first portion of the conductive structure comprising silver chloride.

EMBODIMENT 36 can include or can optionally be combined with the subject matter of one or any combination of EMBODIMENTS 33-35, to optionally include the first portion of the conductive structure comprising a silver chloride coating portion of silver metal.

EMBODIMENT 37 can include or can optionally be combined with the subject matter of one or any combination of EMBODIMENTS 33-36, to optionally include the conductive structure comprising one or more metal-coated threads.

EMBODIMENT 38 can include or can optionally be combined with the subject matter of one or any combination of EMBODIMENTS 33-37, to optionally include the conductive structure comprising one or more silver-coated threads.

EMBODIMENT 39 can include or can optionally be combined with the subject matter of one or any combination of EMBODIMENTS 33-38, to optionally include the hydrogel body comprising a water-based gel with electrically conductive particles dispersed therein.

EMBODIMENT 40 can include or can optionally be combined with the subject matter of one or any combination of EMBODIMENTS 33-39, to optionally include a stabilizing coating applied onto the hydrogel body.

EMBODIMENT 41 can include or can optionally be combined with the subject matter of EMBODIMENT 40, to optionally include the stabilizing coating comprising poly-2-hydroxyethylacrylate.

EMBODIMENT 42 can include or can optionally be combined with the subject matter of one or any combination of EMBODIMENTS 40 and 41, to optionally include the stabilizing coating comprising a coating material that forms a crosslinked network with a hydrogel material of the hydrogel body.

EMBODIMENT 43 can include or can optionally be combined with the subject matter of one or any combination of EMBODIMENTS 33-42, to optionally include the hydrogel body being wash stable.

EMBODIMENT 44 can include or can optionally be combined with the subject matter of one or any combination of EMBODIMENTS 33-43, to optionally include the hydrogel body being dehydratable and rehydratable.

EMBODIMENT 45 can include or can optionally be combined with the subject matter of one or any combination of EMBODIMENTS 33-44, to optionally include a framing layer in contact with the hydrogel body opposite the conductive structure.

EMBODIMENT 46 can include or can optionally be combined with the subject matter of one or any combination of EMBODIMENTS 32-45, to optionally include the electrical signal of at least one of the plurality of textile-based hydrogel electrodes comprising at least one of: an electrooculogram corresponding to a corneo-retinal standing potential of an eye; an electroencephalogram corresponding to neurological electrical activity; an electrocardiogram corresponding to cardiac electrical activity; and an electromyogram corresponding to electrical activity of one or more muscles.

EMBODIMENT 47 can include or can optionally be combined with the subject matter of one or any combination of EMBODIMENTS 32-46, to optionally include a textile-based pressure sensor coupled to the support scaffold so that when the support scaffold is worn by the subject the textile-based pressure sensor is positioned proximate to a blood vessel of the subject.

EMBODIMENT 48 can include or can optionally be combined with the subject matter of EMBODIMENT 47, to optionally include the textile-based pressure sensor comprising a textile-based ion-conductive layer positioned between a pair of textile-based conductive layers.

EMBODIMENT 49 can include or can optionally be combined with the subject matter of EMBODIMENT 48, to optionally include the ion-conductive layer comprising a fabric sheet coated with an alkoxy silane containing a positively charged quaternary ammonium moiety and a counterion.

EMBODIMENT 50 can include or can optionally be combined with the subject matter of one or any combination of EMBODIMENTS 47-49, to optionally include a transverse conductivity across the pressure sensor being proportional to a pressure applied to the pressure sensor.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A textile-based hydrogel electrode comprising:
a textile-based backing layer;
a conductive structure coupled to the textile-based backing layer;

a hydrogel body comprising a hydrogel material in contact with at least a first portion of the conductive structure; and a stabilizing coating covering the hydrogel material of at least a portion of the hydrogel body, wherein the first portion of the conductive structure and the hydrogel material form an ionic interface configured to generate an electrical signal through the conductive structure corresponding to a biopotential change proximate to the textile-based hydrogel electrode.

2. A textile-based hydrogel electrode according to claim 1, wherein the first portion of the conductive structure comprises silver chloride.

3. A textile-based hydrogel electrode according to claim 1, wherein the conductive structure comprises one or more metal-coated threads.

4. A textile-based hydrogel electrode according to claim 1, wherein the hydrogel material comprises a water-based gel with electrically conductive particles dispersed therein.

5. A textile-based hydrogel electrode according to claim 1, wherein the stabilizing coating comprises poly-2-hydroxyethylacrylate.

6. A textile-based hydrogel electrode according to claim 1, wherein the stabilizing coating comprises a coating material that partially diffuses into the hydrogel material of the hydrogel body and forms a crosslinked network with the hydrogel material.

7. A textile-based hydrogel electrode according to claim 1, wherein the electrical signal comprises at least one of: an electrooculogram corresponding to a corneo-retinal standing potential of an eye; an electroencephalogram corresponding to neurological electrical activity; an electrocardiogram corresponding to cardiac electrical activity; and an electromyogram corresponding to electrical activity of one or more muscles.

8. A wearable biopotential measuring device comprising:
a support scaffold configured for wearing by a subject; and
a plurality of electrodes coupled to the scaffold so that when the support scaffold is worn by the subject, each of the plurality of electrodes are positioned proximate to a corresponding specified bodily structure of the subject, wherein each of the plurality of electrodes is configured to generate an electrical signal corresponding to a biopotential change of the corresponding specified bodily structure,
wherein at least one of the electrodes comprises a textile-based hydrogel electrode comprising:
a textile-based backing layer;
a conductive structure coupled to the textile-based backing layer;
a hydrogel body comprising a hydrogel material in contact with at least a first portion of the conductive structure; and
a stabilizing coating covering the hydrogel material of at least a portion of the hydrogel body,
wherein the first portion of the conductive structure and the hydrogel material form an ionic interface that is configured to generate the electrical signal corresponding to the biopotential change of the corresponding bodily structure.

9. A wearable biopotential measuring device according to claim 8, wherein the first portion of the conductive structure comprises silver chloride.

10. A wearable biopotential measuring device according to claim 8, wherein the hydrogel material comprises a water-based gel with electrically conductive particles dispersed therein.

11. A textile-based hydrogel electrode according to claim 1, further comprising a hydrophobic coating on at least a portion of the textile-based backing layer.

12. A textile-based hydrogel electrode according to claim 11, wherein the hydrophobic coating comprises poly(heptadecafluorodecyl acrylate).

13. A textile-based hydrogel electrode according to claim 1, further comprising a fabric-based framing layer positioned on top of the hydrogel body.

14. A wearable biopotential measuring device according to claim 8, wherein the conductive structure comprises one or more metal-coated threads.

15. A wearable biopotential measuring device according to claim 8, wherein the stabilizing coating comprises poly-2-hydroxyethylacrylate.

16. A wearable biopotential measuring device according to claim 8, wherein the stabilizing coating comprises a coating material that partially diffuses into the hydrogel material of the hydrogel body and forms a crosslinked network with the hydrogel material.

17. A wearable biopotential measuring device according to claim 8, wherein the electrical signal comprises at least one of: an electrooculogram corresponding to a corneo-retinal standing potential of an eye; an electroencephalogram corresponding to neurological electrical activity; an electrocardiogram corresponding to cardiac electrical activity; and an electromyogram corresponding to electrical activity of one or more muscles.

18. A wearable biopotential measuring device according to claim 8, wherein the textile-based hydrogel electrode further comprises a hydrophobic coating on at least a portion of the textile-based backing layer.

19. A wearable biopotential measuring device according to claim 18, wherein the hydrophobic coating comprises poly(heptadecafluorodecyl acrylate).

20. A wearable biopotential measuring device according to claim 8, wherein the textile-based hydrogel electrode further comprises a fabric-based framing layer positioned on top of the hydrogel body.

* * * * *